(12) United States Patent
Pioch et al.

(10) Patent No.: US 12,012,608 B2
(45) Date of Patent: *Jun. 18, 2024

(54) TRANSGENIC MAIZE PLANT EXHIBITING INCREASED YIELD AND DROUGHT TOLERANCE

(71) Applicant: KWS SAAT SE & Co. KGaA, Einbeck (DE)

(72) Inventors: Karl Pioch, Gottingen (DE); Wolfgang Koch, Einbeck (DE); Stefan Meldau, Gottingen (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/046,988

(22) Filed: Oct. 17, 2022

(65) Prior Publication Data

US 2023/0250443 A1   Aug. 10, 2023

Related U.S. Application Data

(63) Continuation of application No. 16/481,727, filed as application No. PCT/EP2018/052315 on Jan. 30, 2018, now Pat. No. 11,505,802.

(30) Foreign Application Priority Data

Jan. 30, 2017  (EP) .................................. 17153839

(51) Int. Cl.
*C12N 15/82* (2006.01)
*C12N 9/44* (2006.01)
*C12P 5/02* (2006.01)
*C12P 7/10* (2006.01)

(52) U.S. Cl.
CPC ....... *C12N 15/8261* (2013.01); *C12N 9/2451* (2013.01); *C12N 15/8273* (2013.01); *C12P 5/023* (2013.01); *C12P 7/10* (2013.01); *C12Y 302/01026* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 4,962,028 A | 10/1990 | Bedbrook et al. | |
| 5,188,642 A | 2/1993 | Shah et al. | |
| 5,352,605 A | 10/1994 | Fraley et al. | |
| 5,510,474 A | 4/1996 | Quail et al. | |
| 5,641,876 A | 6/1997 | McElroy et al. | |
| 6,020,190 A | 2/2000 | Quail et al. | |
| 6,054,574 A | 4/2000 | Quail et al. | |
| 6,878,818 B1 | 4/2005 | Goldsbrough | |
| 6,977,325 B2 | 12/2005 | Jilka et al. | |
| 7,112,665 B1 | 9/2006 | Leemans et al. | |
| 11,505,802 B2 * | 11/2022 | Pioch .................. | C12N 9/2451 |
| 2013/0227724 A1 | 8/2013 | Abramson et al. | |

FOREIGN PATENT DOCUMENTS

| | | |
|---|---|---|
| EP | 0 335 528 A2 | 10/1989 |
| EP | 0 388 186 A1 | 9/1990 |
| WO | 84/02913 A1 | 8/1984 |
| WO | 91/02071 | 2/1991 |
| WO | 93/21334 A1 | 10/1993 |
| WO | 95/06128 | 3/1995 |
| WO | 96/38567 | 12/1996 |
| WO | 97/04103 | 2/1997 |

OTHER PUBLICATIONS

Bei Li et al., "Constitutive expression of cell wall invertase genes increases grain yield and starch content in maize", Plant Biotechnology Journal, vol. 11, No. 9, Aug. 9, 2013, pp. 1080-1091.

Albacete Alfonso et al., "Ectopic overexpression of the cell wall invertase gene CIN1 leads to dehydration avoidance in tomato", Journal of Experimental Botany, vol. 66, No. 3, Feb. 2015, pp. 863-878.

von Schweinichen et al., "Expression of a plant cell wall invertase in roots of *Arabidopsis* leads to early flowering and an increase in whole plant biomass", Plant Biology, 2005, vol. 7, No. 5, pp. 469-475.

International Search Report and Written Opinion dated Mar. 14, 2018, issued in corresponding Application No. PCT/EP2018/052315.

Hasegawa et al. "The complete sequence of soybean chiorotic mottle virus DNA and the identification of a novel promoter", Nucleic Acids Research, 1989, vol. 17, No. 23, pp. 9993-10013.

(Continued)

*Primary Examiner* — Brent T Page
(74) *Attorney, Agent, or Firm* — Troutman Pepper Hamilton Sanders LLP

(57) ABSTRACT

The present invention is directed to a transgenic maize plant or a part thereof comprising as transgene a nucleic acid capable of expressing a cell wall invertase or a functional part thereof, preferably a *Chenopodium rubrum* cell wall invertase or a functional part thereof, wherein as a result of the expression of the cell wall invertase or a functional part thereof the transgenic maize plant exhibits an enhanced tolerance to abiotic stress and/or an increased yield, to a method of producing such transgenic maize plant, to method of enhancing the tolerance to abiotic stress of a maize plant and/or of increasing yield potential of a maize plant, to a nucleic acid capable of expressing a cell wall invertase or a functional part thereof, preferably a *Chenopodium rubrum* cell wall invertase or a functional part thereof, to a vector comprising such nucleic acid, the use of the nucleic acid or vector for enhancing the tolerance to abiotic stress of a maize plant, for increasing yield potential of a maize plant and/or for protecting a maize plant against abiotic stress, and to a method for production of ethanol or methane from transgenic maize plant or a part thereof of the invention.

8 Claims, 21 Drawing Sheets

Figure 1A:
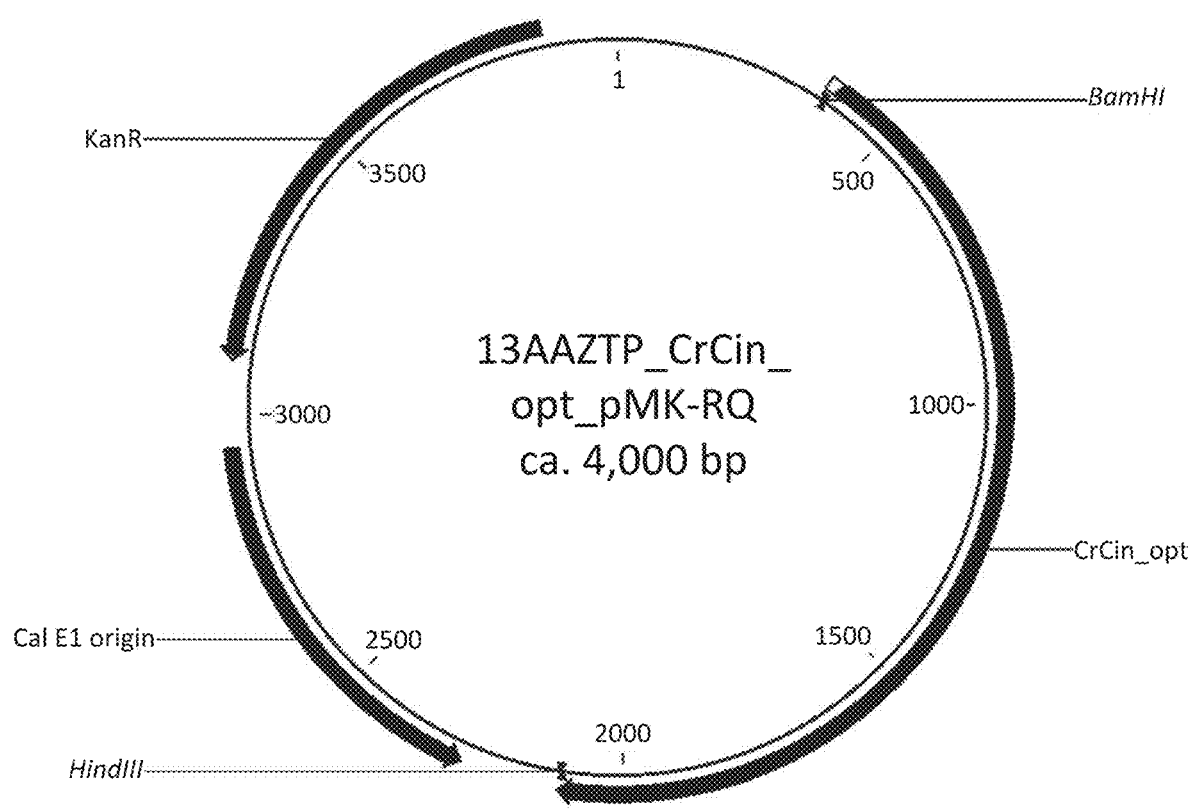

Specification includes a Sequence Listing.

(56) References Cited

OTHER PUBLICATIONS

Franck et al., Nucleotide Sequence of Cauliflower Mosaic Virus DNA, Cell, 1980, vol. 21, pp. 285-294.

Gatz et al., "Stringent repression and homogeneous de-repression by tetracycline of a modified CaMV 35S promoter in intact transgenic tobacco plants", The Plant Journal, 1992, vol. 2, No. 3, pp. 397-404.

Knopf, "Crown-Gall and Agrobacterium tumefaciens: Survey of a Plant-Cell-Transformation System of Interest to Medicine and Agriculture", Subcellular Biochemistry, 1979, Chapter 3, Roodyn Ed., pp. 143-173.

Hiel et al., "Efficient transformation of rice (*Oryza sativa* L.) mediated by Agrobacterium and sequence analysis of the boundaries of the T-DNA", The Plant Journal, 1994, vol. 6, No. 2, pp. 271-282.

Bruce et al., "Photoregulation of a phytochrome gene promoter from oat transferred into rice by particle bombardment", Proc. Natl. Acad. Sci. USA, 1989, vol. 86, No. 24, pp. 9692-9696.

Klein et al., "Transformation of Microbes, Plants and Animals by Particle Bombardment", Bio/technology, 1992, vol. 10, No. 3, pp. 286-291.

Chang et al., "High Frequency Transformation of Bacillus subtilis Protoplasts by Plasmid DNA", Mol. Gen. Genet., 1979, vol. 168, No. 1, pp. 111-115.

Mercenier et al., "Strategies for the development of bacterial transformation systems", Biochimie, 1988, vol. 70, No. 4, pp. 503-517.

Gordon et al., "DNA-mediated genetic transformation of mouse embryos and bone marrow—a review", Gene, 1985, vol. 33, No. 2, pp. 121-136.

Zhang et al., "Efficient Transformation of Tobacco by Ultrasonication", Bio/Technology, 1991, vol. 9, pp. 996-997.

Deshayes et al., "Liposome-mediated transformation of tobacco mesophyll protoplasts by an *Escherichia coli* plasmid", The EMBO Journal, 1985, vol. 4, No. 11, pp. 2731-2737.

Christou et al., "Stable transformation of soybean by electroporation and root formation from transformed callus", Proc Natl. Acad. Sci. U.S.A., 1987, vol. 84, pp. 3962-3966.

Hain et al., "Uptake, integration, expression and genetic transmission of a selectable chimaeric gene by plant protoplasts", Mol. Gen. Genet., 1985, vol. 199, pp. 161-168.

Draper et al., "TI Plasmid Homologous Sequences Present in Tissues from Agrobacterium Plasmid-transformed Petunia Protoplasts", Plant Cell Physiol., 1982, vol. 23, No. 3, pp. 451-458.

White et al., "A cassette containing the bar gene of Streptomyces hydroscopicus: a selectable marker for Plant transformation", Nucleic Acids Research, 1990, vol. 18, No. 4, p. 1062.

Hatfield et al., "Temperature extremes: Effect on plant growth and development", Weather and Climate Extremes, 2015, vol. 10, pp. 4-10.

O'Toole et al., "Response of leaf water potential, stomatal resistance, and leaf rolling to water stress", Plant Physiology, 1980, vol. 65, No. 3, pp. 428-432.

Roitsch et al., "Induction of Apoplastic Invertase of Chenopodium rubrum by D-Glucose and a Glucose Analop and Tissue Specific Expression Suggest a Role in Sink-Source Regulation", Plant Physiol., 1995, vol. 108, pp. 285-294.

Munns et al., "Mechanisms of salinity tolerance", Annual Review of Plant Biology, 2008, vol. 59, pp. 651-681.

Faize et al., "Involvement of cytosolic ascorbate peroxidase and Cu/Zn-superoxide dismutase for improved tolerance against drought stress", Journal of Experimental Botany, 2011, vol. 62, No. 8, pp. 2599-2613.

Skirycz et al., "Survival and growth of *Arabidopsis* plants given limited water are not equal", Nature Biotechnology, 2011, vol. 29, No. 3, pp. 212-214.

Ambavaram et al., "Coordinated regulation of photosynthesis in rice increases yield and tolerance to environmental stress", Nature Communications, 2014, vol. 5, Article 5302, 38 pages.

Bledsoe et al., "The role of Tre6P and SnRK1 in maize early kernel development and events leading to stress-induced kernel abortion", BMC Plant Biology, 2017, vol. 17, No. 74, 17 pages.

\* cited by examiner

FIG 16

| Location | Location 1 | Location 2 | Location 3 | Location 4 | Location 5 | All locations |
|---|---|---|---|---|---|---|
| Line 4 | 91.1 | 98.3 | 106.5 | 77.6 | 73.09 | 89.3 |
| Line 5 | 82.4 | 94.03 | 84.1 | 74.5 | 73.17 | 82.03 |
| Line 1 | 89.08 | 86.12 | 77.7 | 74.006 | 66.01 | 79.75 |
| Line 3 | 75.39 | 79.79 | 84.6 | 80.8 | 74.73 | 78.91 |
| Line 6 | 78.9 | 83.5 | 87.2 | 95.4 | 103.9 | 88.7 |
| Line 2 | 61.5 | 88.2 | 74.7 | 85.15 | 92.48 | 79.4 |

TRANSGENIC MAIZE PLANT EXHIBITING INCREASED YIELD AND DROUGHT TOLERANCE

CROSS-REFERENCE TO RELATED APPLICATIONS

This application is a continuation application of U.S. application Ser. No. 16/481,727, filed Jul. 29, 2019, which is a U.S. National Phase of International Patent Application No. PCT/EP2018/052315, filed Jan. 30, 2018, which claims priority to European Patent Application No. 17153839.0, filed Jan. 30, 2017, all of which are herein incorporated by reference in their entireties.

SEQUENCE LISTING

This application contains a Sequence Listing which has been submitted in electronically in XML format and is hereby incorporated by reference in its entirety. Said XML copy, created on Oct. 12, 2022, is named 245761_000187_SL.xml, and is 12,161 bytes in size.

Plants are exposed during their life term to a series of abiotic stress conditions such as heat stress, frost stress, chilling stress, salinity stress, drought stress etc. Such stress conditions are important limiting factors for plant growth and productivity. Thus, exposure of plants for example to heat and/or drought conditions may typically lead to reduction of yields of plant material such as leaves, seeds, fruits and other edible or usable products. Such yield reductions represent with economically important plants such as maize, rice or wheat an important economical factor, whereby especially in many underdeveloped countries such yield reductions may result in food shortages which endanger the food supply of the population.

Maize is the most widely produced crop in the world. This cereal is grown in at least 164 countries around the world with a total production of more than 1 billion metric tons. Maize is grown at latitudes varying from the equator to slightly above 50 degrees north and south, from sea level to over 3000 meters elevation, in cool and hot climates, and with growing cycles ranging from 3 to 13 months. It is therefore of importance for the food supply of the world population that the supply with maize plants remains at high level. However, especially regions with extreme weather conditions such as extreme heat, extreme cold, extreme wetness, extreme drought etc. run danger that the food supply is not ensured, which, in view of obvious weather changes in the last years, has become an even more critical subject. Moreover, the importance of maize as a renewable resource has increased in the last years in view of the fact that the combustion of resources such as oil, coal, and natural gas contributes to the warming of the world climate and resources are needed which, due their regrowth, do not contribute to a negative $CO_2$ balance.

In view of this, it is a scientific demand to provide maize plants and other crop plants which brave the climate in all its forms and other abiotic factors and, despite heat, chilling, drought, salinity, wetness etc. consistently provide high yields.

Cell wall invertases, also called extracellular invertases, are crucial enzymes for an appropriate metabolism, growth and differentiation of plants. They work by hydrolysis of sucrose into glucose and fructose outside cells which are subsequently imported into target cells by monosaccharide transporters. The monosaccharides do not only serve as a source of carbon and energy for plants, but they are also key signaling molecules that potentially regulate cell division, growth, differentiation, metabolism and resource allocation in plants. Cell wall invertases are regarded as crucial to supply sink tissues with carbohydrates via an apoplastic pathway.

Cell wall invertases are known in the art as potentially increasing the grain yield and biomass of certain plants. Thus, Li et al. (Li B. et. al., Plant Biotechnology Journal, 2013, 11, 1080-1091) disclose the constitutive overexpression of three cell wall invertase genes (AtCWIN1, OsGIF1 and ZmMn1) in transgenic maize plants leading to an increase in grain yield. Schweinichen and Büttner (Schweinichen C. and Büttner M., Plant Biol. (Stuttg), 2005, 7, 469-475) disclose the root-specific expression of *Chenopodium rubrum* cell wall invertase in *Arabidopsis* leading to early flowering and increased biomass of the whole plant, probably due to an extensive root growth. Albacete A. et al., Journal of Experimental Botany, 2015, 66, 863-878 disclose that fruit-specific expression of *Chenopodium rubrum* cell wall invertase in transgenic tomato can lead to improved drought tolerance, however they did not observed an increased shoot weight or leaf area, i.e. biomass.

Despite these successes of increasing plant yields, there is still a need to provide economically important plants which produce high biomass yield, even under adverse abiotic conditions.

To address this issue, the present inventors succeeded in developing maize plants which overcome disadvantages of previous maize plants in that these maize plants show both, an enhanced drought tolerance and biomass production. Thereby, the present inventors introduced *Chenopodium rubrum* cell wall invertase (CrCIN) into maize plants and found that these maize plants produced increased yield and had increased tolerance to drought.

The invention is described in the following, with reference to the claims.

In the following, the present invention is described in detail. The features of the present invention are described in individual paragraphs. This, however, does not mean that a feature described in a paragraph stands isolated from a feature or features described in other paragraphs. Rather, a feature described in a paragraph can be combined with a feature or features described in other paragraphs.

The term "comprise/es/ing", as used herein, is meant to "include or encompass" the disclosed features and further features which are not specifically mentioned. The term "comprise/es/ing" is also meant in the sense of "consist/s/ing of" the indicated features, thus not including further features except the indicated features. Thus, the product and method of the present invention may be characterized by additional features in addition to the features as indicated.

In a first aspect, the present invention relates to a transgenic maize plant comprising as transgene i) a nucleic acid capable of expressing a *Chenopodium rubrum* cell wall invertase (CrCIN) or a functional part thereof, ii) the nucleic acid capable of expressing the *Chenopodium rubrum* cell wall invertase or the functional part thereof of item i) which is modified by the degeneration of the genetic code, iii) a nucleic acid capable of expressing a cell wall invertase or a functional part thereof having at least 80%, 85%, 90%, 95%, 96%, 97%, 98%, or 99% amino acid identity or at least 70%, 80%, 85%, 90%, 95%, 96%, 97%, 98%, 99% or 100% amino acid homology to the *Chenopodium rubrum* cell wall invertase or the functional part thereof of item i), or iv) a nucleic acid capable of hybridizing under stringent conditions with a complementary sequence of the nucleic acid of any one of items i) to iii), whereby the nucleic acid of item iv) is capable of expressing a cell wall invertase, wherein as a result of the expression of the *Chenopodium rubrum* cell wall invertase or a functional part thereof or a homolog thereof the transgenic maize plant exhibits an enhanced tolerance to abiotic stress and/or an increased yield, optionally as compared to a reference.

In an embodiment thereof, the nucleic acid is derived from the nucleic acid of any one of items i) to iv) by codon optimization.

In an embodiment of the above, the nucleic acid of item i) comprises the nucleic acid sequence of SEQ ID NO: 3 or encodes the amino acid sequence of SEQ ID NO: 4.

In an embodiment of the above, the transgenic maize plant comprises as transgene an expression cassette comprising the nucleic acid.

In an embodiment of the above, the nucleic acid or the expression cassette is stably integrated into the genome of the maize plant or is transiently expressed in the maize plant, for example is present in the maize plant on a vector.

In an embodiment of the above, the expression of the nucleic acid is controlled by a promoter, preferably a constitutive promoter.

In an embodiment of the above, the abiotic stress is selected from drought, salinity, heat or chilling and/or the yield is biomass yield or grain yield.

The present inventors have surprisingly demonstrated that *Chenopodium rubrum* cell wall invertase is effective in enhancing in a maize plant tolerance to drought stress and/or of increasing yield of a maize plant. This is surprising insofar, as the present inventors also demonstrated that the same gene introduced into wheat plants were not effective in increasing biomass or grain yield. This shows that the effect of cell wall invertases in general and specifically of *Chenopodium rubrum* cell wall invertase in a heterologous setting is not predictable.

Thus, by introducing the gene coding for *Chenopodium rubrum* cell wall invertase the present inventors were able to enhance in a maize plant tolerance to abiotic stress and/or to increase (biomass) yield of a maize plant under normal and/or stress conditions. Specifically, the present inventors showed that the gene coding for *Chenopodium rubrum* cell wall invertase introduced into a maize plant was expressed and expression of the gene resulted in an enhanced production of leaves, in the production of higher plants and in the production of maize plants with a higher drought resistance as compared to a reference.

The transgenic maize plant of the present invention expresses *Chenopodium rubrum* cell wall invertase (Cr-CIN). The gene encoding the CIN1 cell wall invertase derived from *Chenopodium rubrum* is known in the art and is, e.g. characterized by the accession number as available from the NCBI database (National Centre for Biotechnology Information; National Library of Medicine 38A, Bethesda, MD20894, USA; www.ncbi.nih.gov) under the accession number X81792.1 (SEQ ID NO: 5) encoding the protein with the accession number CAA57389.1 (SEQ ID NO: 2). *Chenopodium rubrum* cell wall invertase and the gene encoding the cell wall invertase are not restricted to SEQ ID NOs: 1 and 2, but include any *Chenopodium rubrum* cell wall invertase naturally expressed by *Chenopodium rubrum* and the gene encoding the *Chenopodium rubrum* cell wall invertase. Moreover, the transgenic maize plant of the present invention comprises a nucleic acid that expresses a "homolog" of a *Chenopodium rubrum* cell wall invertase. A "homolog", as defined herein, is a cell wall invertase which has an amino acid identity to a *Chenopodium rubrum* cell wall invertase, as exemplarily identified by SEQ ID NO: 2, of at least 80%, 85%, 90%, 95%, 96%, 97%, 98%, or 99%, or which has an amino acid homology to a *Chenopodium rubrum* cell wall invertase, as exemplarily identified by SEQ ID NO: 2, of at least 70%, 80%, 85%, 90%, 95%, 96%, 97%, 98%, 99% or 100%. Thereby, "amino acid homology" refers to identical or homologous amino acids. Homologous amino acid residues have similar chemical-physical properties, for example, amino acids belonging to a same group: aromatic (Phe, Trp, Tyr), acid (Glu, Asp), polar (Gln, Asn), basic (Lys, Arg, His), aliphatic (Ala, Leu, lie, Val), with a hydroxyl group (Ser, Thr), or with a short lateral chain (Gly, Ala, Ser, Thr, Met). It is expected that substitutions between such homologous amino acids do not change a protein phenotype (conservative substitutions). Alternatively, a "homolog" is a cell wall invertase which is encoded by a nucleic acid which is capable of hybridizing under stringent conditions with the complementary sequence of the nucleic acid coding for a *Chenopodium rubrum* cell wall invertase, such as identified by SEQ ID NO: 2, or with the complementary sequence of the nucleic acid coding for a cell wall invertase which has amino acid identity or amino acid homology to *Chenopodium rubrum* cell wall invertase, as identified above.

The *Chenopodium rubrum* cell wall invertase, such as identified by SEQ ID NO: 2, or a homolog thereof confers on the maize plant an enhanced tolerance to abiotic stress and/or the maize plant harboring a nucleic acid coding for *Chenopodium rubrum* cell wall invertase, such as identified by SEQ ID NO: 2, or a homolog thereof has an increased yield, optionally as compared to a reference. Preferably, *Chenopodium rubrum* cell wall invertase, such as identified by SEQ ID NO: 2, or a homolog thereof may not be capable of conferring on a wheat plant into which it has been transformed tolerance to abiotic stress and/or of increasing the yield of a wheat plant, more specifically *Chenopodium rubrum* cell wall invertase or a homolog thereof may not be capable of increasing wheat plant height or grain yield.

As used herein, a "functional part" of a *Chenopodium rubrum* cell wall invertase or of a homolog thereof refers to any part of the protein which has the same activity as full-length *Chenopodium rubrum* cell wall invertase such as identified SEQ ID NO: 2, namely the functional part hydrolyses sucrose into glucose and fructose. Moreover, the functional part confers on the maize plant an enhanced tolerance to abiotic stress and/or the maize plant harboring the functional part has an increased yield, optionally as compared to a reference. Preferably, the functional part may not be capable of conferring on a wheat plant into which it has been transformed tolerance to abiotic stress and/or of increasing the yield of a wheat plant, more specifically the functional part may not be capable of increasing wheat plant height or grain yield.

As used herein, the term "maize plant" means any plant of the species *Zea mays*.

As used herein, the term "nucleic acid" may be a DNA, a RNA or a hybrid of DNA and RNA. Preferably, the DNA is double-stranded. It may be a genomic DNA comprising intron sequences and possibly regulatory sequences in the 5' and/or 3' region or a cDNA without intron sequences. The term "nucleic acid", as used herein, comprises nucleic acids which encode *Chenopodium rubrum* cell wall invertases or a functional part thereof or a homolog thereof, as defined above. Moreover, the term "nucleic acid" comprises a nucleic acid which is modified by the degeneration of the genetic code of a nucleic acid encoding a naturally occurring *Chenopodium rubrum* cell wall invertase.

As used herein, the term "nucleic acid" is also meant to include a part of a nucleic acid encoding *Chenopodium*

*rubrum* cell wall invertase or a homolog thereof, whereby the part of a nucleic acid encodes a functional part of a *Chenopodium rubrum* cell wall invertase or a homolog thereof, as defined above.

The term "degeneration of the genetic code" refers to the degeneracy of codons which is a term known in the art and means the redundancy of the genetic code exhibited as the multiplicity of three-base pair codon combinations that specify a given amino acid. Thus, the codon coding for an amino acid can be specifically changed without that the amino acid is changed. This results in a variety of nucleic acids coding for the same *Chenopodium rubrum* cell wall invertase.

The percentage of "sequence identity" or "sequence homology", as used herein, refers to the percentage of amino acid residues which are identical or homologous, respectively, in corresponding positions in two optimally aligned sequences. It is determined by comparing two optimally aligned sequences over a comparison window, where the fragment of the amino acid sequence in the comparison window may comprise additions or deletions (e.g., gaps or overhangs) as compared to a reference sequence (which does not comprise additions or deletions) for optimal alignment of the two sequences. The percentage is calculated by determining the number of positions at which the identical or homologous amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith T. F. and Waterman M. S., Add APL Math, 1981, 2, 482-489, by the homology alignment algorithm of Needleman S. B. and Wunsch C. D., J. Mol. Biol., 1970, 48, 443-453, by the search for similarity method of Pearson W. R. and Lipman D. J., PNAS, 1988, 85, 2444-2448, by the algorithm of Karlin S. and Altschul S. F., PNAS, 1990, 87, 2264-2268, modified by Karlin S. and Altschul S. F., PNAS, 1993, 90, 5873-5877, or by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by inspection. GAP and BESTFIT are preferably employed to determine the optimal alignment. Typically, the default values of 5.00 for gap weight and 0.30 for gap weight length may be used.

As used herein, the term "hybridize(s)(ing)" refers to the formation of a hybrid between two nucleic acid molecules via base-pairing of complementary nucleotides. The term "hybridize(s)(ing) under stringent conditions" means hybridization under specific conditions. An example of such conditions includes conditions under which a substantially complementary strand, such as a strand composed of a nucleotide sequence having at least 80% complementarity, hybridizes to a given strand, while a less complementary strand does not hybridize. Alternatively, such conditions refer to specific hybridizing conditions of sodium salt concentration, temperature and washing conditions. As an example, highly stringent conditions comprise incubation at 42° C., 50% formamide, 5×SSC (150 mM NaCl, 15 mM trisodium citrate), 50 mM sodium phosphate, 5×Denhardt's solution, 10× dextran sulphate, 20 mg/ml sheared salmon sperm nucleic acid and washing in 0.2×SSC at about 65° C. (SSC stands for 0.15 M sodium chloride and 0.015 M trisodium citrate buffer). Alternatively, highly stringent conditions may mean hybridization at 68° C. in 0.25 M sodium phosphate, pH 7.2, 7% SDS, 1 mM EDTA and 1% BSA for 16 hours and washing twice with 2×SSC and 0.1% SDS at 68° C. Further alternatively, highly stringent hybridisation conditions are, for example: Hybridizing in 4×SSC at 65° C. and then multiple washing in 0.1×SSC at 65° C. for a total of approximately 1 hour, or hybridizing at 68° C. in 0.25 M sodium phosphate, pH 7.2, 7% SDS, 1 mM EDTA and 1% BSA for 16 hours and subsequent washing twice with 2×SSC and 0.1% SDS at 68° C.

The present inventors showed that the nucleic acid encoding a *Chenopodium rubrum* cell wall invertase or a functional part thereof or a homolog thereof can be expressed in a maize plant. The expressed cell wall invertase confers on the maize plant an enhanced tolerance to abiotic stress and/or the maize plant exhibits an increased yield. "Tolerance to abiotic stress" means that the introduction and expression of *Chenopodium rubrum* cell wall invertase or a functional part thereof or a homolog thereof in a maize plant renders the maize less susceptible to adverse abiotic conditions, whereby typical stress symptoms due to the adverse abiotic factors do not occur or occur to a lesser degree than in a reference. Alternatively or additionally, introduction and expression of *Chenopodium rubrum* cell wall invertase or a functional part thereof or a homolog thereof in a maize plant increases the yield of the maize plant, optionally as compared to a reference. "Increased yield", as used herein, means that the transgenic maize plant exhibits an increased growth rate under normal conditions which do not produce stress to the plant or abiotic stress conditions, optionally as compared to a reference. An increased growth rate comprises an increased mass production of the whole plant or a part thereof such as an increased mass production of the overground part of the plant, e.g. of stem, leaves, florescence, cobs, and/or grains etc., and/or an increased mass production of the underground part of the plant. The "increased mass production" may include any part of the transgenic maize plant and refers in particular to the stem, leaves, cobs and/or grains. "Increased yield" also comprises a prolonged growth and survival, also resulting in an increased mass production.

As used herein, the term "reference" may refer to a maize plant of the same genotype as the transgenic maize plant of the present invention whereby the reference does not comprise the transgene encoding *Chenopodium rubrum* cell wall invertase or a functional part thereof or a homolog thereof. Reference experiments including (a) reference maize plant(s) may be conducted parallel to the experiments for testing the properties of the transgenic maize plants of the present invention. However, reference experiments may also be conducted at a different time point under comparable conditions and the results may be compared after all experiments are finished. Alternatively, the "reference" may be a specific (pre)determined measure of yield or of a symptom such as the percentage of leaves showing leaf rolling symptom under drought conditions which characterizes a maize plant as having tolerance to an abiotic stress factor or as having no tolerance to an abiotic stress factor. For example, a reference measure may be an already determined measure or a publicly available measure which provides to the skilled person a threshold measure and helps him/her to decide that a transgenic maize plant is tolerant or not tolerant to an abiotic stress factor or has an increased yield, dependent of whether the measure of the transgenic maize plant is below or above this measure. Based on this reference measure (e.g. number of leaves with rolling symptoms), the skilled person can then identify a maize plant as being tolerant to a stress factor if the maize plant has a lower number of leaves with rolling symptoms than the reference measure or as having increased yield if the maize plant indicates a higher yield than the reference measure. Thereby, the maize plant(s) used for establishing the reference measure does not need to be, but may be, a maize plant of same genotype as the transgenic maize plant. For example, the reference maize plant(s) may be (a) maize plant(s) which has(ve) a degree of tolerance to an abiotic stress factor which reflects the average tolerance degree of a population of maize plants adapted to a specific environment. The skilled person who wants to develop a maize plant better adapted to the specific environment may use this measure as reference and develop a transgenic maize plant which exhibits a better measure and which is, therefore, better adapted to the specific environment. Or the reference maize plant(s) may be (a) maize plant(s) with a certain degree of tolerance to an abiotic stress factor, and it is an object to generate a transgenic maize plant which has a higher degree of tolerance to the abiotic factor. Likewise, the skilled person may want to develop a transgenic maize plant with a high yield under specific conditions, and may use the comparison with a reference measure to determine whether the transgenic maize plant meets the object.

For determination whether a transgenic maize plant shows "tolerance to abiotic stress" or "increased yield", CrCIN transcript and/or protein expression and/or expression level from the transgene may be determined, according to methods known in the art. Thus, the determination whether a transgenic maize plant harboring a *Chenopodium rubrum* cell wall invertase or a functional part thereof or a homolog thereof has tolerance to abiotic stress or increased yield does not necessarily require the comparison with a reference. The present inventors have found that introduction and expression of the *Chenopodium rubrum* cell wall invertase results in an increase in yield and increased tolerance to abiotic stress factors, as is shown in the exemplary part of the present specification.

The term "abiotic stress" or "abiotic stress conditions" refers to stress conditions for the maize plant arising from abiotic, i.e. non-living, factors. Such abiotic factors include drought, salinity (concentration of salt), heat or chilling. While not being want to be bound by the following, it may be assumed that the effect of the *Chenopodium rubrum* cell wall invertase or a functional part thereof or a homolog thereof in the maize plant is related to an increased carbohydrate pool, which is generated due to the increased activity of *Chenopodium rubrum* cell wall invertase or a functional part thereof or a homolog thereof in the maize plant where the enzyme is overexpressed. Sugars which are generally known to have a protective effect against osmotic stress may result in a molecular cellular phenotype in the maize plant which protects the maize plant from stress conditions such as drought, salinity and/or heat conditions at which osmotic events play a role. Moreover, sugars which are generally known to have protective effect against chilling or frost temperature impacts may result in a molecular cellular phenotype which protects the maize plant from stress conditions such as chilling.

In a preferred embodiment of the present invention, the nucleic acid as comprised by the maize plant according to the present invention is codon optimized. Once a cell wall invertase has been selected for transformation of a maize plant, the codons may be modified and adapted to the specific requirements of the host in order to maximize expression. Codon optimization of a nucleic acid for expression in heterologous host cells is known to those skilled in the art. There are numerous commercial providers that have developed algorithms that consider relevant transcription and translation optimization parameters and deliver a nucleic acid sequence configured to the requirements of nucleic acid and host. For example, codon optimization can be effected by the GeneOptimizer™ software, GeneArt, ThermoFisher Scientific. A preferred nucleic acid, as comprised by the present invention, is the codon optimized sequence of SEQ ID NO: 3 derived from SEQ ID NO: 1 encoding the polypeptide of SEQ ID NO: 4. The codons are especially adapted to the codon usage in maize plants.

The term "expression of" or "expressing" means (1) the transcription of a nucleic acid as comprised by the present invention into an RNA or mRNA and/or (2) the translation of the RNA or mRNA into *Chenopodium rubrum* cell wall invertase or a functional part thereof or a homolog thereof.

As used herein, an "expression cassette" is a nucleic acid molecule which is composed of one or more open reading frames or genetic sequences which are expressed into (a) protein(s) in a maize plant into which the expression cassette has been introduced and regulatory element(s) in the 5' and optionally 3' position controlling their expression. Thus, an expression cassette may contain a promoter regulatory sequence, also designated promoter, operably linked to an open reading frame or another genetic sequence, and a 3' terminator regulatory region that may contain a polyadenylation site. The promoter directs the machinery of the cell to make RNA and/or protein. The regulatory element(s) may be from the cell wall invertase nucleic acid which is introduced into the maize plant or may be from different genes, as long as the regulatory element(s) is(are) able to function in the maize plant. Moreover, the regulatory element(s) in the 5' position may be derived from the same gene as the regulatory element(s) in the 3' position or may be derived from different genes. As used herein, "operably linked" means that expression of the linked nucleic acid sequences occurs in the maize plant. An expression cassette may be part of a vector used for cloning and introducing the nucleic acid into a cell.

For introducing the nucleic acid molecule capable of expressing a *Chenopodium rubrum* cell wall invertase or a homolog thereof or a functional part thereof into a cell, the nucleic acid molecule or the expression cassette harboring the nucleic acid may be inserted into a vector. Vectors which harbor a nucleic acid molecule are known to those in the art. In addition to the nucleic acid molecule, the vector may comprise regulatory element(s) in the 5' and optionally in the 3' positions which are able to function in a maize plant. The regulatory element(s) are preferably heterologous to the *Chenopodium rubrum* cell wall invertase or a functional part thereof or a homolog thereof. Thus, the vector may comprise a promoter regulatory sequence operably linked to the nucleic acid molecule, and optionally a terminator regulatory sequence. Preferably, the vector is a shuttle vector for transformation into *Agrobacterium tumefaciens* and subsequent transfer of the nucleic acid molecule encoding a *Chenopodium rubrum* cell wall invertase or a functional part thereof or homolog thereof into maize plant cells by infection of the maize plant by the transformed *Agrobacterium tumefaciens*. More preferably, the vector is a binary vector which is a standard tool in the transformation of higher plants mediated by *Agrobacterium tumefaciens*. It is composed of the borders of T nucleic acid, multiple cloning sites, replication functions for *Escherichia coli* and *Agrobacterium tumefaciens*, selectable marker genes, reporter genes, and other accessory elements that can improve the efficiency of and/or give further capability to the system. Another more preferred vector is a super-binary vector that carries additional virulence genes from a Ti plasmid, and exhibits very high frequency of transformation, which is valuable for recalcitrant plants such as cereals. A number of useful vectors are available in the art. Especially preferred is a binary vector which comprises the ubiquitin promoter of maize (e.g., U.S. Pat. Nos. 5,510,474 A, 6,020,190 A, 6,054,574 A, 6,878,818 B1, 6,977,325 B2) and the nos terminator sequence of *Agrobacterium tumefaciens* or the 35S terminator sequence of cauliflower mosaic virus as transcription regulatory sequences and preferably extended by a herbicide resistance gene (e.g. pat gene for conferring Basta resistance (e.g., U.S. Pat. No. 7,112,665 B1)) and/or the spectinomycin resistance gene as selectable marker genes.

According to the invention, the term "promoter regulatory sequence" or "promoter" is intended to mean any promoter of a gene that can be expressed in a maize plant. Such promoter may be a promoter which is naturally expressed in the maize plant or is of fungal, bacterial, or viral origin. The promoter may include a constitutive promoter, a tissue specific promoter, or an inducible promoter, whereby constitutive expression is preferred. A number of suitable promoters are available in the art. For example, a constitutive promoter useful in the invention is the ubiquitin promoter from maize. Another promoter is the Act-1 promoter from rice (e.g., U.S. Pat. No. 5,641,876 A). The NCR promoter from soybean chlorotic mottle virus (SoyCMV) (Hasegawa, A., et al. "The complete sequence of soybean chlorotic mottle virus DNA and the identification of a novel promoter." *Nucleic acids research* 17.23 (1989): 9993-10013.) has also been shown to be useful in monocotyledonous plants. Further useful promoters are the 35S CaMV (Franck A. et al., 1980, Cell 21:285-294) and the 19S CaMV promoter from cauliflower mosaic virus (U.S. Pat. No. 5,352,605; WO 84/02913) or plant promoters like those from the Rubisco small subunit (U.S. Pat. No. 4,962,028).

The promoter used in the method of the invention may be an inducible promoter. An inducible promoter is a promoter that is capable of directly or indirectly activating transcription of a nucleic acid sequence in response to an inducer. In the absence of an inducer, the nucleic acid sequence will not be transcribed. Inducible expression may be desirable. Stimuli for inducible promoters are of different kind and include environmental conditions such as light, temperature and/or abiotic stress conditions such as water stress, salinity stress conditions, cold stress or heat stress. Other types of stimuli for inducible promoters are hormones (for example gibberellin, abscisic acid, jasmonic acid, salicylic acid, ethylene, auxin) or chemicals (tetracycline, dexamethasone, estradiol, copper, ethanol, and benzothiadiazol). Thus, the expression of *Chenopodium rubrum* cell wall invertase or a functional fragment thereof or a homolog thereof under specific inducive conditions, preferably under abiotic stress conditions, results in the protection of the maize plant by preventing stress symptoms and allowing the formation of mass. Inducible promoters are e.g. promoters which are benzyl sulfonamide inducible (EP 0 388 186), tetracyclin inducible), Gatz C. et al., Plant J. 2, 1992: 397-404), abscisic acid inducible (EP 0 335 528) or ethanol or cyclohexenol inducible (WO 93/21334).

In addition to a promoter sequence, an expression cassette or vector may also contain a terminator downstream of the structural gene to provide for efficient termination. According to the invention, the term "terminator" or "terminator regulatory sequence" is intended to mean any such sequence that is functional in terminating expression of a nucleic acid in a maize plant, also optionally comprising polyadenylation sequences. The terminator may be obtained from the same gene as the promoter sequence or may be obtained from a different gene. Thus, it may be of viral origin such as the CaMV 35S terminator which is the preferred one, of bacterial origin such as the octopine synthase or the nopaline synthase terminator of *Agrobacterium tumefaciens*, or of plant origin such as a histone terminator. Polyadenylation sequences include, but are not limited to, the *Agrobacterium* octopine synthase signal.

The term "introducing" or "introduction", as used herein, means inserting a nucleic acid into a maize plant by any means known in the art, such as "transformation" using non-viral introduction methods or "transduction" using viral-mediated gene transfer. For introducing the nucleic acid molecule into a maize plant, numerous methods are known in the art (see, for example, Miki et al., "Procedures for Introducing Foreign nucleic acid into Plants" in Methods in Plant Molecular Biology and Biotechnology, Glick, B. R. and Thompson, J. E. Eds. (CRC Press, Inc., Boca Raton, 1993), pages 67-88). In addition, expression vectors and in vitro culture methods for plant cell or tissue transformation and regeneration of plants are available (see, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993), pages 89-119).

A preferred method applied in the present invention is transformation of the nucleic acid molecule, expression cassette or vector harboring the nucleic acid molecule by the use of bacteria of the *Agrobacterium* genus, preferably by infection of cells or tissues of a maize plant with *A. tumefaciens* (Knopf U. C., 1979, Subcell. Biochem. 6: 143-173; Shaw C. H. et al., 1983, Annu. Rev. Genet. 16: 357-384; Tepfer M. and Casse-Delbart F., 1987, Microbiol. Sci. 4(1): 24-28). For example, the transformation of maize plant cells or tissues with *Agrobacterium tumefaciens* is carried out according to the protocol described by Hiei Y. et al. (1994, Plant J. 6(2): 271-282).

Another method for introducing a nucleic acid into a maize plant is the biolistic transformation method, wherein cells or tissues are bombarded with particles onto which the nucleic acid, expression cassette or vector as comprised by the invention are adsorbed (Bruce W. B. et al., 1989, Proc. Natl. Acad. Sci. USA 86(24): 9692-9696; Klein T. M. et al., 1992, Biotechnology 10(3): 286-291; U.S. Pat. No. 4,945, 050). A further method is the widely used protoplast transformation. Therefore, plant cells are separated by pectinases and subsequently, the cell wall is degraded to generate protoplasts. For transformation, polyethylene glycol may be added or electroporation may be applied. Other methods are bringing the plant cells or tissues into contact with polyethylene glycol (PEG) and the nucleic acid, expression cassette or vector of the invention (Chang S. and Cohen S. N., 1979, Mol. Gen. Genet. 168(1): 111-115; Mercenier A. and Chassy B. M., 1988, Biochimie 70(4): 503-517). Electroporation is another method, which consists of subjecting the cells or tissues to be transformed and the nucleic acid, expression cassette or vector as comprised by the invention to an electric field (Andreason G. L. and Evans G. A., 1988, Biotechniques 6(7): 650-660; Shigekawa K. and Dower W. J., 1989, Aust. J. Biotechnol. 3(1): 56-62). Another method consists of directly injecting the nucleic acid, expression cassette or vector as comprised by the invention into the cells or the tissues by microinjection (Gordon and Ruddle, 1985, Gene 33(2): 121-136). Another method for physical delivery of a nucleic acid to plants is sonication of target cells (Zhang et al., Bio/Technology 9: 996 (1991)). Alternatively, liposome or spheroplast fusion may be used to introduce the nucleic acid, expression cassette or vector as comprised by the invention into plants (Deshayes et al., EMBO J., 4: 2731 (1985), Christou et al., Proc Natl. Acad. Sci. U.S.A. 84: 3962 (1987)). Direct uptake of a nucleic acid into protoplasts using $CaCl_2$ precipitation, polyvinyl alcohol or poly-L-ornithine has also been reported (Hain et al., Mol. Gen. Genet. 199: 161 (1985); Draper et al., Plant Cell Physiol. 23: 451 (1982)).

The selection step for identifying a transgenic maize plant comprising the nucleic acid can be carried out via a selectable gene present on the vector, as referred to above. The selectable gene may comprise an operably linked promoter regulatory sequence and possibly a terminator regulatory sequence that are functional in maize cells. Among the selectable markers that can be used in the present invention, reference is made to genes for resistance against antibiotics, such as the spectinomycin resistance gene, the hygromycin phosphotransferase gene, the neomycin phosphotransferase II gene inducing resistance against kanamycin, or the aminoglycoside 3'-adenyltransferase gene, the bar gene (White J. et al., Nucl. Acids Res., 1990, 18: 1062) for tolerance to bialaphos, the EPSPS gene (U.S. Pat. No. 5,188,642) for tolerance to glyphosate or the HPPD gene (WO 96/38567) for tolerance to isoxazoles, genes encoding identifiable enzymes, such as the GUS enzyme, GFP protein or genes encoding pigments or enzymes regulating pigment production in the transformed cells. Such selectable marker genes are in particular described in patent applications WO 91/02071, WO 95/06128, WO 96/38567, and WO 97/04103. In a preferred embodiment, the spectinomycin resistance gene and the pat gene are used as the selectable genes on a binary vector in the present invention.

Marker gene free transformation is another alternative to transfer the nucleic acid, expression cassette or vector, as referred to above, into a maize plant.

In one embodiment, the nucleic acid or expression cassette is stably integrated into the genome of the transgenic maize plant, preferably into a chromosome of the plant such as the nuclear, plastid and/or mitochondrial chromosome. Integration can, however, also occur into an extrachromosomal element. By stable integration into the genome of a plant, the nucleic acid sequences can be passed to subsequent generations of the transgenic plant. Stable integration and passing to next maize plant generations is preferred in the present invention. Using the *Agrobacterium tumefaciens* mediated transformation method of plants as the preferred transformation method, the *Chenopodium rubrum* cell wall invertase nucleic acid is stably integrated into the maize plant genome. Alternatively, the nucleic acid or expression cassette or vector harboring the nucleic acid or expression cassette may be converted into an autonomous replicon. Alternatively, the nucleic acid molecule or expression cassette is present within the plant cell on the vector used to introduce the nucleic acid molecule and is not stably integrated into the genome of the plant, or the nucleic acid is transiently expressed such as transformed mRNA. Therefore, the nucleic acid sequences may not be passed to subsequent generations of the maize plant.

The term "heterologous", as used herein, refers to conditions wherein molecules are present in environments under which they are not naturally present. For example, a nucleic acid molecule which is expressed in a host cell in which it is not naturally expressed is a heterologous nucleic acid. Consequently, the host cell is then a heterologous host cell. Heterologous regulatory elements are those which are linked to nucleic acid molecules to which they are not naturally linked.

A "transgenic maize plant", as used herein, refers to a maize plant which contains a nucleic acid capable of expressing a *Chenopodium rubrum* cell wall invertase or a functional part thereof or a homolog thereof integrated into its nuclear genome or organelle genome or being present on an autonomous replicon or on the vector used to introduce the nucleic acid as comprised by the present invention or being present as mere coding sequence without other elements. This term encompasses further the offspring generations such as T1, T2 or consecutive generations, as well as crossbreeds thereof with non-transgenic or other transgenic plants. The transgenic maize plant advantageously contains at least one copy of the nucleic acid as comprised by the invention.

Expression of *Chenopodium rubrum* cell wall invertase or a functional part or a homolog thereof in a maize plant enhances tolerance to abiotic stress conditions. Preferred "abiotic stress" against which the transgenic maize plant of the present invention exhibits enhanced tolerance includes drought, salinity (concentration of salt), heat and/or chilling.

"Drought" or "drought conditions" mean conditions of water deficiency arising from a long period of low or no water supply (water stress condition), especially conditions that adversely affect growing and/or living conditions of a maize plant. Under drought conditions, the plant will show symptoms of injury such as wilting, leaf browning and/or leaf rolling, growth is hampered and the plant will eventually die. Drought conditions can be generated by growing a maize plant of the V2, V3, V4, V5, V6, V7, or V8 (according to Leaf Collar Method described below) stage for one week in ¼ strength Hoagland Solution and then treating it for one day in 25% PEG6000. "Tolerance to drought", as used herein, may mean that the transgenic maize plant shows significantly reduced leaf rolling symptoms under drought conditions such as treatment of plants with Hoagland Solution and 25% PEG6000. "Significantly reduced" means that the percentage of leaves with rolling symptoms is reduced as compared to a reference by at least 20, 30, 40, 50, 60, 70, 80, 90, 95 or 100%. Alternatively, a maize plant is tolerant to drought if at the most 60, 50, 40, 30, 20, 10 or 5 or less % of the leaves of the maize plant in the V2, V3, V4, V5, V6, V7, V8 and/or VT (fully mature plant with inflorescence) stage show rolling symptoms if kept under drought conditions.

"Salinity" or "salinity conditions" mean conditions of high concentration of salt such as 100 mM NaCl solution for irrigation, especially in the air and/or in the soil, especially conditions that adversely affect growing and/or living conditions of a maize plant. The ability of plants to tolerate salt is determined by multiple biochemical pathways that facilitate retention and/or acquisition of water, protect chloroplast functions, and maintain ion homeostasis. Essential pathways include those that lead to synthesis of osmotically active metabolites, specific proteins, or certain free radical scavenging enzymes that control ion and water flux and support scavenging of oxygen radicals or chaperones. The cause of cell wall invertases to protect a maize plant from adverse salinity effects may lie in their ability to synthesize osmotically active compounds. Under salinity conditions, the yield of the maize plant will be lower than under non-salinity conditions. Under extended and/or very high salinity conditions, the maize plant will eventually die. "Tolerance to salinity" may mean that the transgenic plant of the V2, V3, V4, V5, V6, V7, or V8 stage survives and/or grows under salinity conditions as compared to a reference which does no longer grow or grows to a lesser degree, whereby under very high salinity conditions and/or over an extended period of salinity, the maize plant will eventually die. By "survives" is meant that the transgenic maize plant survives for a longer period of time, such as at least 10, 11, 12, 13 or more days, than the reference. By "grows" is meant that the increase in yield of the whole maize plant or of parts thereof such as stem, leaves, cobs or grains is at least 20, 30, 40, 50, 60, 70, 80, 90 or 100%, as compared to the yield of a control.

"Heat" or "heat conditions" mean conditions under high temperature such as ca. 33-40° C. at ear level along a 15-days pre-anthesis period, especially conditions that adversely affect growing and/or living conditions of a maize plant. Rate of plant growth and development is dependent upon the temperature surrounding the plant. Extreme heat events occurring during the vegetation period seems to have the most dramatic impact on plant productivity; whereby extreme heat may cause reduction in grain yield. In general, extreme high temperatures during the reproductive stage may affect pollen viability, fertilization, and grain formation. Chronic exposures to extreme temperatures during the pollination stage of initial grain set will reduce grain yield potential. Acute exposure to extreme events may be most detrimental during the reproductive stages of development (Hatfield J. L. and Prueger J. H., 2015, Weather and Climate Extremes, 10: 4-10). Bearing in mind that temperature and extreme temperature events are expected to increase due to the warming of world climate, the development of maize plants with an enhanced tolerance to heat stress conditions seems to be an urgent need. "Tolerance to heat", as used herein, may mean that the transgenic plant of the V2, V3, V4, V5, V6, V7, or V8 and pollination stage survives and/or grows under heat conditions as compared to a reference which does no longer grow or grows to a lesser degree. By "survives" is meant that the transgenic maize plant survives for a longer period of time, such as at least 10, 11, 12, 13 or more days, than the reference. By "grows" is meant that the increase in yield of the whole maize plant or of parts thereof such as stem, leaves, cobs or grains is at least 20, 30, 40, 50, 60, 70, 80, 90 or 100%, as compared to the yield of a control.

"Chilling" or "chilling conditions" mean conditions under chilling temperature such as under 10° C. but above the freezing point, especially conditions that adversely affect growing and/or living conditions of a maize plant. Chilling may cause damage (chlorosis) and interrupts the pathways for nutrients and water to flow. Under chilling conditions, the plant will produce less yield. "Tolerance to chilling" may mean that the transgenic plant of the V2, V3, V4, V5, V6, V7, V8 (????) stage survives and/or grows under chilling conditions as compared to a reference which does no longer grow or grows to a lesser degree. By "survives" is meant that the transgenic maize plant survives for a longer period of time than the reference. By "grows" is meant that the increase in yield of the whole maize plant or of parts thereof such as stem, leaves, cobs or grains is at least 20, 30, 40, 50, 60, 70, 80, 90 or 100%, as compared to the yield of a control.

It will be understood by those skilled in the art that, due to the large number of different maize varieties that are grown under a broad spectrum of climate and other abiotic conditions, it is difficult to indicate specific values with respect to drought, salinity, heat or chilling, such as days of drought, degree of salinity or height of temperature, which guide the skilled person under which conditions tolerance to an abiotic factor should be tested. For example, maize plants with high drought tolerance will need stronger drought conditions than maize plants with a lower drought tolerance in order to assess whether the corresponding transgenic maize plant shows higher tolerance or will produce higher yield. Therefore, the test conditions will depend on the maize plant used for inserting the transgene and/or on the purpose for which the transgenic maize plant will be used.

Due to the fact that introduction and expression of *Chenopodium rubrum* cell wall invertase results in an increase in yield of the transgenic maize plant under normal and drought conditions and in a drought tolerant phenotype, it is not necessarily required that a transgenic maize plant which expresses a *Chenopodium rubrum* cell wall invertase or a functional part thereof or a homolog thereof is compared to a reference, as referred to herein, if it should be determined whether the transgenic maize plant has tolerance to abiotic stress such as drought, salinity, heat and/or chilling. It may be sufficient to determine expression of the *Chenopodium rubrum* cell wall invertase or a functional part thereof or a homolog thereof, e.g. by determining the amount of transcript or protein, in order to detect that tolerance to the abiotic stress factors drought, salinity, heat and/or chilling exists.

Resistance to an abiotic stress factor may be determined by exposing the transgenic maize plant to an abiotic stress factor and determining the degree of stress factor symptoms and/or yield. The obtained measures may be compared to a reference. Resistance may also be detected by determining expression or expression level of the transcript expressed from the transgene as comprised by the present invention.

In a second aspect, the invention relates to a plant cell, a tissue, a harvestable part or a seed of the transgenic maize plant of the present invention, wherein the plant cell, the tissue, the part or the seed comprises the transgene as comprised by the present invention.

In principle, any part, tissue or organ of a maize plant is included within the present invention to comprise as a transgene a nucleic acid encoding a *Chenopodium rubrum* cell wall invertase or a functional part thereof or a homolog thereof. Thus, shoot vegetative organs/structures, e.g., leaves, stems, roots, flowers or floral organs/structures, e.g. bracts, sepals, petals, stamens, carpels, anthers or ovules; seed, including embryo, endosperm or seed coat; grain or the mature ovary; plant tissue, e.g. vascular tissue or ground tissue; or cells, e.g. guard cells, egg cells or trichomes; or progeny of the same are included within the present invention. The term "cell" refers to a cell or cell accumulation within the plant as well as to an isolated cell or isolated cell accumulation. A cell may have a cell wall or may be a protoplast. The present invention also relates to a seed which comprises the nucleic acid, expression cassette or vector as comprised by the present invention. Preferably, the seeds of a transgenic maize plant retain the nucleic acid, expression cassette or vector as comprised by the invention, so that the new plants generated from a seed continues to comprise the nucleic acid, expression cassette or vector.

A "harvestable part" is any part of the plant which can be harvested and used by man. Preferably, the harvestable part may be the whole overground part of the maize plant which can be cut, possibly fermented and used as animal food in animal breeding or in biogas plants as energy source for generating energy providing substances such as biofuel such as ethanol or methane. Preferably, the harvestable part may be the cob, especially the grains, which are used for nutrition of man and animal.

In a third aspect, the invention relates to a method of producing a transgenic maize plant, comprising the steps of introducing into at least a cell of a maize plant the nucleic acid or the expression cassette or the vector as comprised by the invention, and regenerating the transgenic maize plant from the at least one cell.

As used herein, "regenerating" or "regeneration" means a process of growing an entire maize plant from a single cell, a group of cells, a part of the maize plant or a tissue of the maize plant.

The skilled person knows methods of introducing nucleic acid into at least a cell of the maize plant and growing a maize plant therefrom. "At least a cell" means a single cell, a group of cells, a part of the maize plant or a tissue of the maize plant.

In a fourth aspect, the invention relates to method of enhancing the tolerance to abiotic stress of a maize plant and/or of increasing yield potential of a maize plant, comprising the steps of introducing into at least a cell of a maize plant the nucleic acid or the expression cassette or the vector as comprised by the invention, and causing expression of the nucleic acid, the expression cassette, or the vector.

As used herein, the term "causing expression" means that under the conditions, under which the plant is kept and/or cultivated, transcription of the nucleic acid introduced into the maize plant occurs. For example, if the promoter is a constitutive promoter, expression occurs consistently, whereas in case the promoter is an inducible promoter, the activity of the promoter can be induced by the presence or absence of specific biotic or abiotic factors.

As used herein, the term "yield potential" means the capability of the transgenic maize plant to increase yield. By expression of a *Chenopodium rubrum* cell wall invertase or a functional part thereof or a homolog thereof, the capability is conferred on the maize plant that its yield can be increased.

In a fifth aspect, the invention relates to the use of the nucleic acid or the expression cassette or the vector as comprised by the invention for enhancing the tolerance to abiotic stress of a maize plant, for increasing yield potential of a maize plant and/or for protecting a maize plant against abiotic stress.

As used herein, "protecting a maize plant against abiotic stress" means conferring resistance against abiotic stress on the maize plant. A resistant maize plant is not damaged by abiotic stress factors or is damaged to a lesser degree as compared to a reference. Resistance may be determined as tolerance to abiotic stress is determined. This includes that resistance may be determined by determining transcript and/or protein expression or expression level from the transgene.

In an embodiment, in the method of the fourth aspect or the use of the fifth aspect the abiotic stress is selected from drought, salinity, heat or chilling, and/or the yield potential is biomass yield potential or grain yield potential The term "biomass yield potential" or "grain yield potential" has the meaning as referred to above with respect to "yield potential", thereby referring to biomass yield or grain yield, respectively.

The term "biomass" generally refers to organic matter derived from a plant. The term "biomass" can be used for a source of energy and does not refer to food or feed. Thus, as used herein, the term "biomass" refers to the parts of the maize plant, usually the overground parts such as the whole overground maize plant, which can be used as an energy source by converting it to various forms of biofuel such as ethanol or methane.

In a sixth aspect, the invention relates to the nucleic acid which is derived from a nucleic acid encoding *Chenopodium rubrum* cell wall invertase or a functional part thereof or a homolog thereof as comprised by the present invention by codon optimization, preferably wherein the nucleic acid comprises the nucleic acid sequence of SEQ ID NO: 3 or encodes the amino acid sequence of SEQ ID NO: 4. The invention also relates to an expression cassette comprising said nucleic acid or a vector comprising said nucleic acid or expression cassette.

In a seventh aspect, the invention relates to a vector comprising the nucleic acid as defined or the expression cassette as defined in the present invention.

In an eighth aspect, the invention relates to a method for production of ethanol or methane comprising the following steps: cutting the transgenic maize plant or harvestable part according to the present invention, optionally treating the cut maize plant or the cut harvestable part with an ensilage agent, optionally storing the cut maize plant or the cut harvestable part optionally treated with an ensilage agent, and producing ethanol or methane from the cut maize plant or the cut harvestable part by anaerobic digestion.

The eighth aspect serves to provide a method by which the transgenic maize plant is used as an energy source for providing biofuel such as ethanol or methane which are used in petrol, for heating, for obtaining electricity etc. The processes for obtaining energy from maize plants are known in the technical field of biogas recovery where cut maize or other plant material is stored and fermented in a process called ensilage with the help of anaerobic bacteria.

Treatment of the cut biomass with an ensilage agent serves to improve the ensilaging result. By adding powerful lactic acid bacteria or other bacteria useful for anaerobic digestion of the biomass and/or chemical agents, undesired bacteria such as butyric acid generating bacteria are inhibited. Chemical agents may be sodium nitrite or hexamine for reducing undesired bacteria such as butyric acid generating bacteria, or sodium benzoate or potassium sorbate for preventing the growth of yeasts and mildews. Thus, failed anaerobic digestions and/or after-warming processes can be prevented and the anaerobic digestion process can be controlled.

By "storing the cut maize plant or cut harvestable part" is meant the placing in a container, silo or pit and compressing it so as to leave as little oxygen as possible or keeping it under anaerobic conditions in order to avoid growth of aerobic bacteria. Storing is preferably performed under suitable conditions regarding suitable temperature, moisture, low or no oxygen etc. to allow anaerobic digestion. The skilled person knows the conditions and devices which are to be used for storage and anaerobic digestion.

The present invention discloses a method of conferring on a maize plant tolerance to abiotic stress, comprising the following steps: introducing into at least a cell of a maize plant a nucleic acid capable of expressing a cell wall invertase or a functional part thereof or a homolog thereof, an expression cassette comprising the nucleic acid or a vector comprising the nucleic acid or the expression cassette, and causing expression of the nucleic acid, the expression cassette, or the vector.

The present invention discloses the use of a nucleic acid capable of expressing a cell wall invertase or a functional part thereof or a homolog thereof, an expression cassette comprising the nucleic acid or a vector comprising the nucleic acid or the expression cassette for conferring on a maize plant tolerance to abiotic stress or for protecting a maize plant against abiotic stress.

The above method or use may comprise as abiotic stress drought, salinity, heat and/or chilling.

The cell wall invertase as referred to in the above mentioned method and use may be any cell wall invertase without being restricted to *Chenopodium rubrum* cell wall invertase or a homolog thereof or a functional part thereof, with the function of hydrolysing sucrose into glucose and fructose outside the cell which are then transported into cells and of conferring on a maize plant tolerance to abiotic stress. These functions also apply to the "part" and "homolog", which are otherwise defined as outlined above. The definitions of the other features as comprised by the method or use such as tolerance, abiotic stress, expression cassette, vector etc. are as comprised herein.

The invention is further explained in the following figures and examples which are included for illustration purposes and are not intended to limit the invention.

FIGURES

Figure 1B:
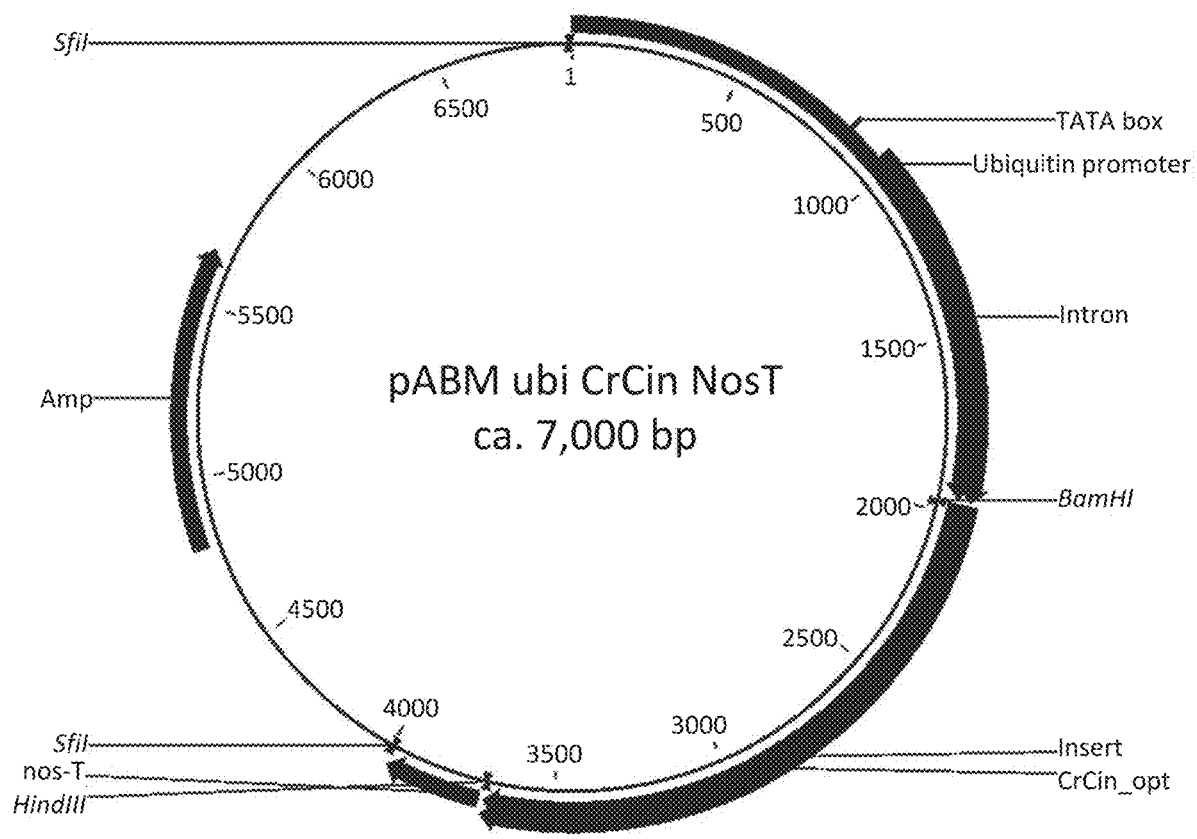
Figure 1C:
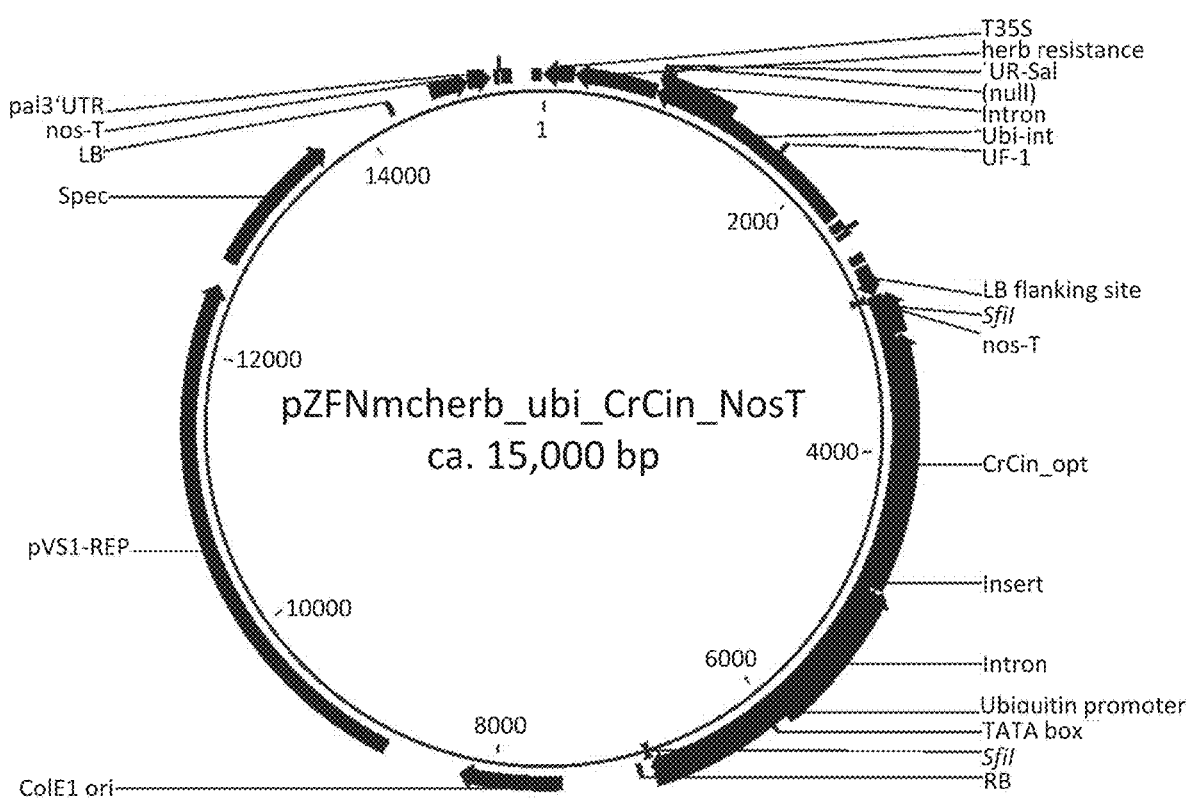

FIG. 1A-C: Vectors used for Cloning CrCIN: Three vectors were used for cloning CrCIN. FIG. 1A: The first vector was received from GeneArt (ThermoScientific) containing a synthesised codon-optimized CrCIN gene (SEQ ID NO: 3). FIG. 1B: This gene was excised using the restriction enzymes BamHI and HindIII and cloned into the shuttle vector pABM containing the cloning cassette (ubi promoter and NosT terminator). FIG. 1C: This entire gene cassette was excised using the marked enzyme SfiI and cloned into the binary vector pZFNmcherb for transformation into *Agrobacterium* and finally maize.

Figure 2:
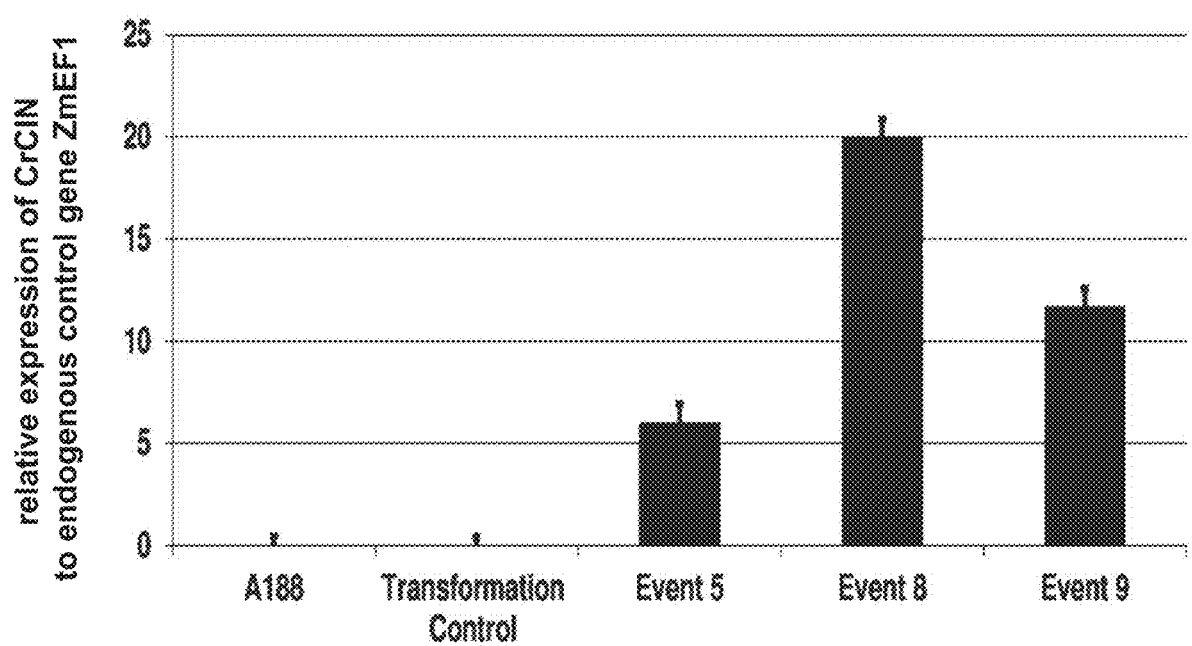

FIG. 2: Expression levels of the homozygous T1 CrCIN plants: RT-qPCR displaying relative expression of selected CrCIN events to endogenous control gene ZmEF1. Both non-transformed A188 and the transformation control (A188 transformed with empty vector) showed no expression, while those A188-lines containing CrCIN as transgene showed CrCIN expression.

Figure 3A:
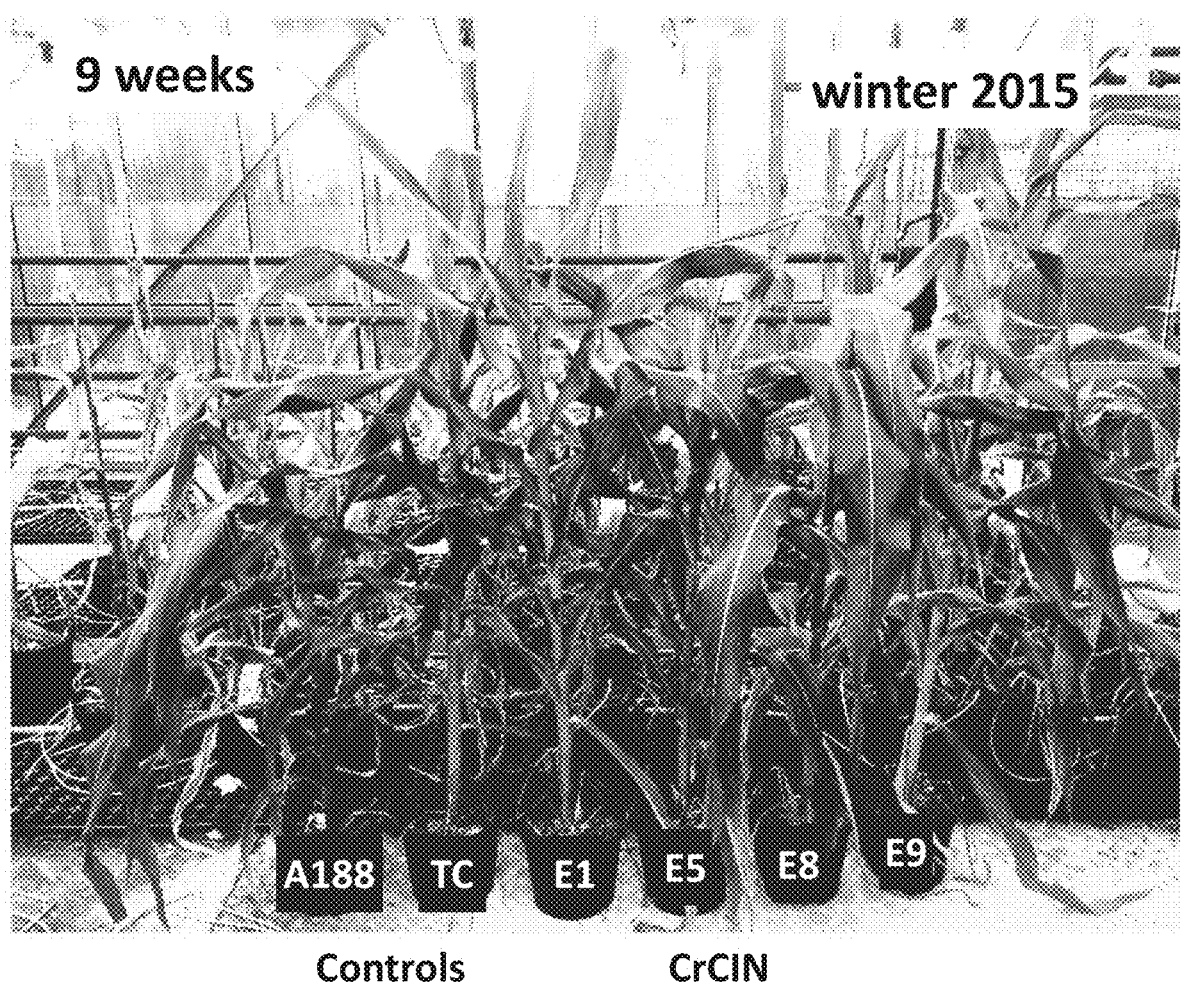
Figure 3B:
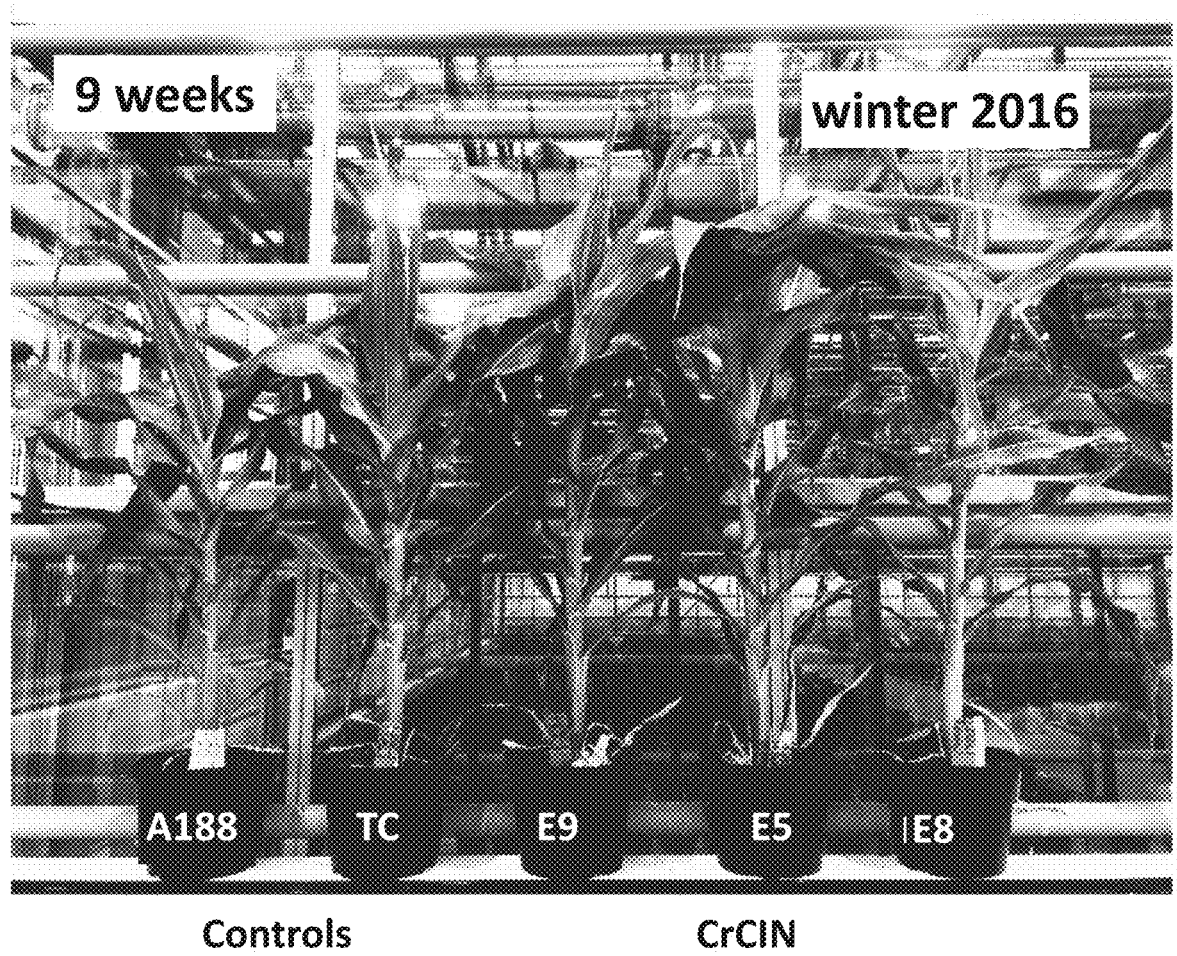

FIG. 3A-3B: T1 CrCIN plants winter 2015 (FIG. 3A) and T2 CrCIN plants winter 2016 (FIG. 3B). Photographs of transgenic CrCIN plants, selected events of Event 1, Event 5, Event 8 and Event 9 (E1, E5, E8 and E9) lined up with 2 controls, A188 WT (wildtype) and TC (transformation control) during 2 growth periods at Week 9. Event 1 is absent from experiment in 2016. All events shown here displayed significant increases in yield (biomass).

Figure 4:
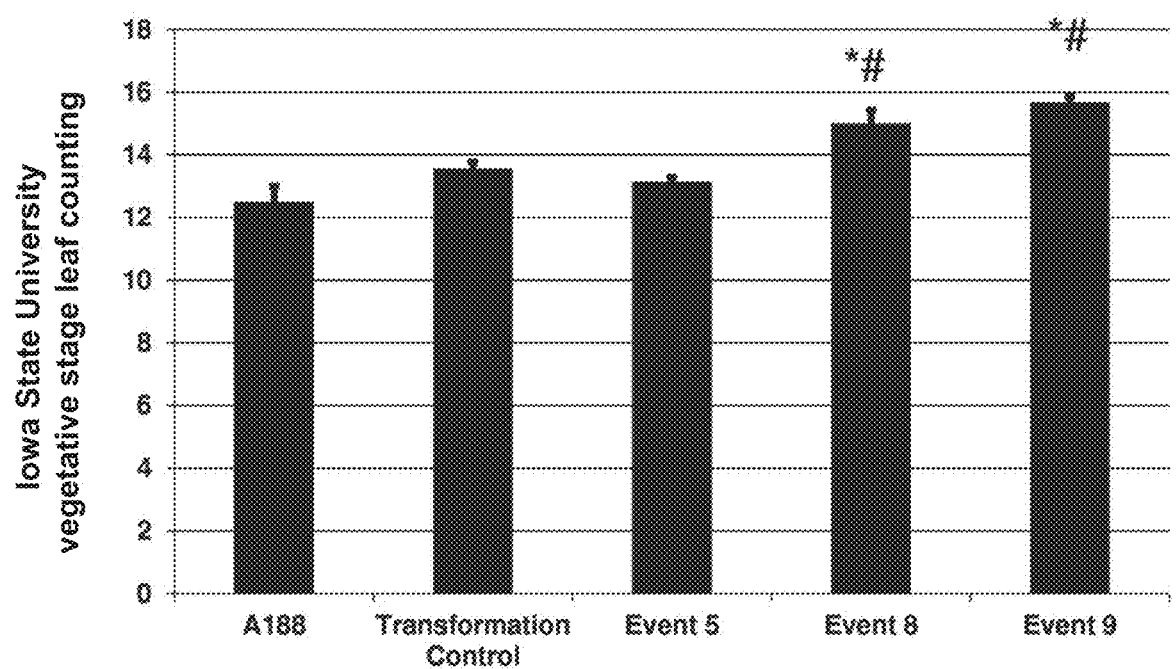

FIG. 4: T1 CrCIN plant physiology measurements at week 8: Yield comparison of transgenic T1 CrCIN events E9, E5 and E8 plants compared to A188 and transformation control plants (n=5) using the Iowa State University Vegetative Stage leaf counting method at 8 weeks after sowing. Plants that were significantly different (student t-test) compared to A188 were marked with an asterisk while plants significantly different to the transformation control were marked with a hash.

Figure 5:
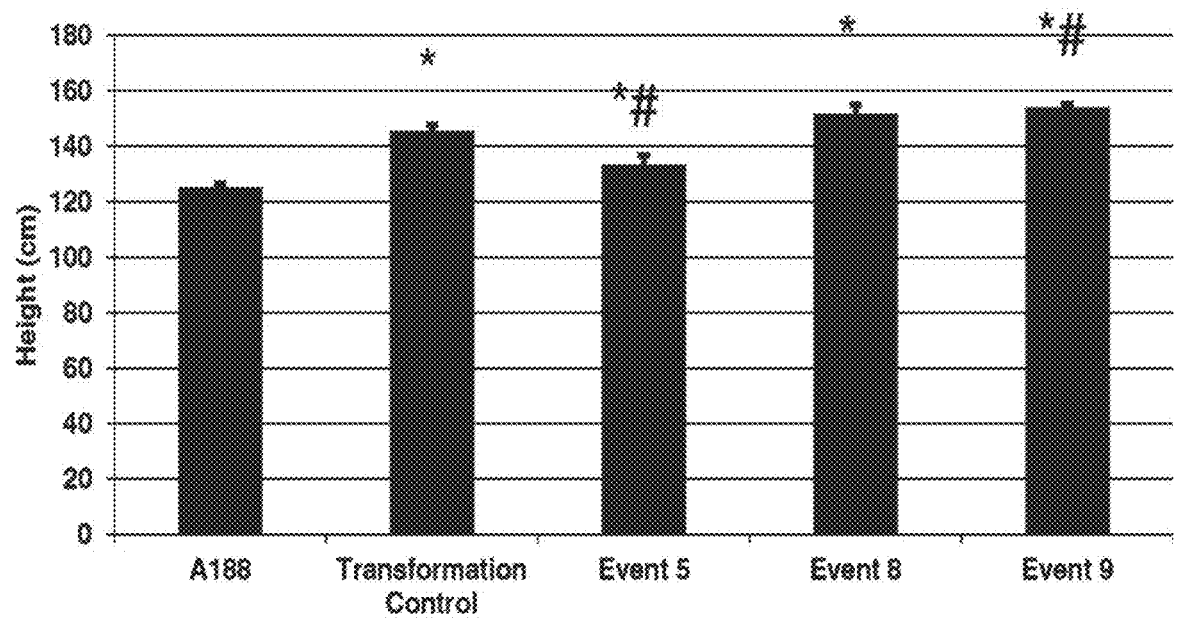

FIG. 5: T1 CrCIN plant physiology measurements at week 8: Plant height comparison of transgenic T1 CrCIN events E9, E5 and E8 plants compared to A188 and transformation control plants (n=5) at 8 weeks after sowing. Plants that were significantly different (student t-test) compared to A188 were marked with an asterisk while plants significantly different to the transformation control were marked with a hash.

Figure 6:
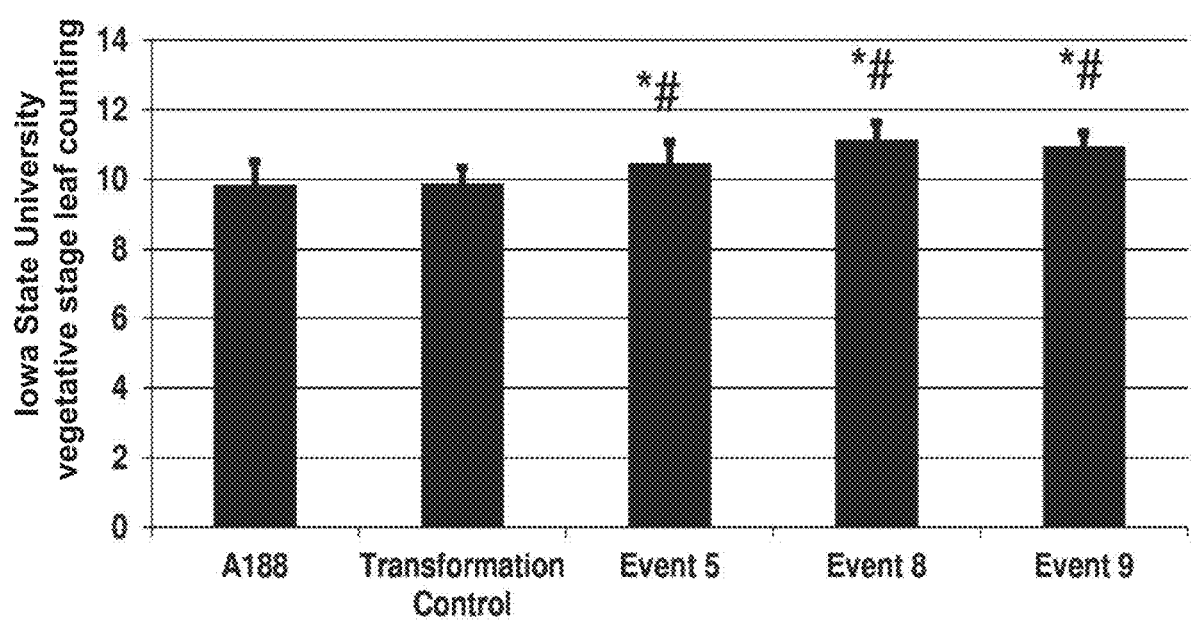

FIG. 6: T2 plant physiology measurements at week 8: Yield comparison of transgenic T2 CrCIN events E9, E5 and E8 plants (n=20) compared to A188 and transformation control plants (n=40) using the Iowa State University Vegetative Stage leaf counting method at 8 weeks after sowing. Plants that were significantly different (student t-test) compared to A188 were marked with an asterisk while plants significantly different to the transformation control were marked with a hash.

Figure 7:
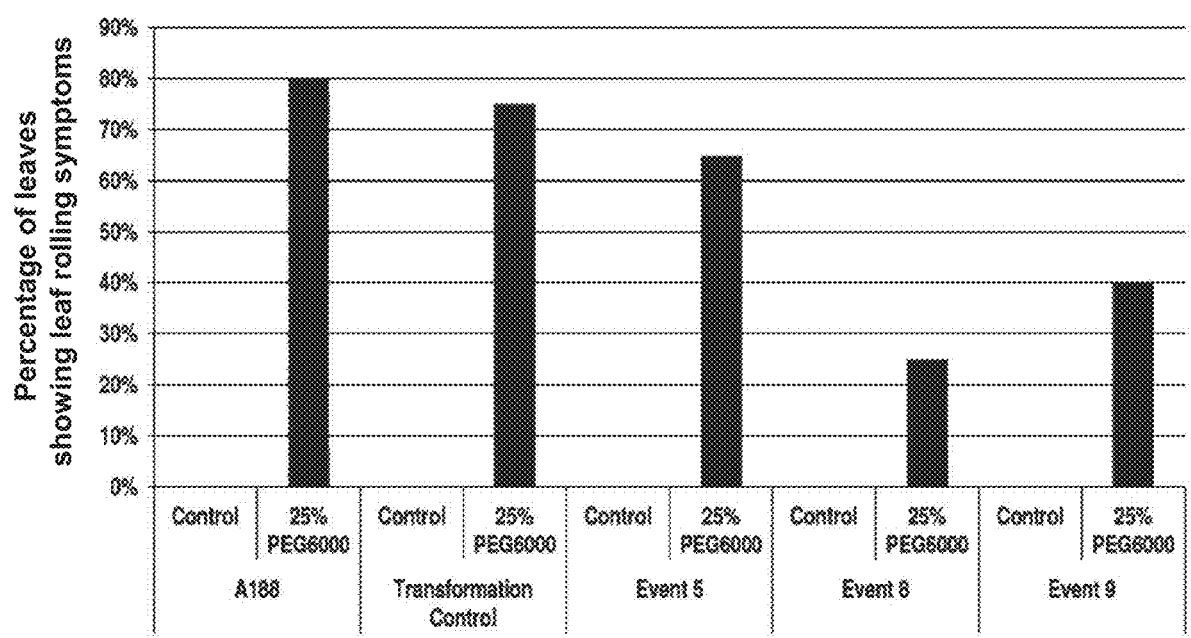

FIG. 7: Experiment 1: CrCIN maize seedlings under simulated drought stress: Graph displaying the percentage of leaves of 25% PEG6000 treated versus untreated plants (n=10) that showed leaf rolling symptoms of leaves. All plants were grown for 1 week in ¼ strength Hoagland Solution and then treated for 1 day in added 25% PEG6000. Both control events showed high levels of leaf rolling. Event 5 showed reduction in leaf rolling symptoms. Event 8 and Event 9 showed a significant reduction in leaf rolling symptoms.

Figure 8:
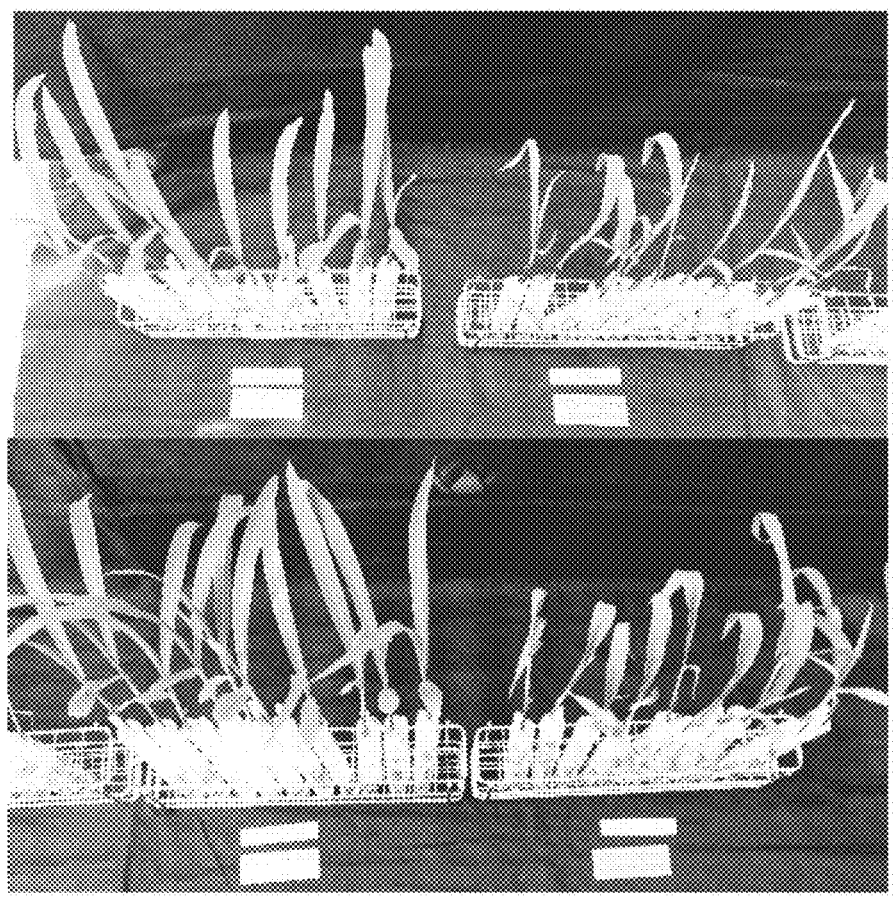

FIG. 8: Experiment 1: CrCIN maize seedlings under simulated drought stress: Photo of Event 8 CrCIN seedlings in ¼ strength Hoagland for 1 week after germination followed by 2 days treatment with 25% PEG6000. Here it can be seen that the leaves of Event 8 show less leaf rolling symptoms than the WT.

Figure 9:
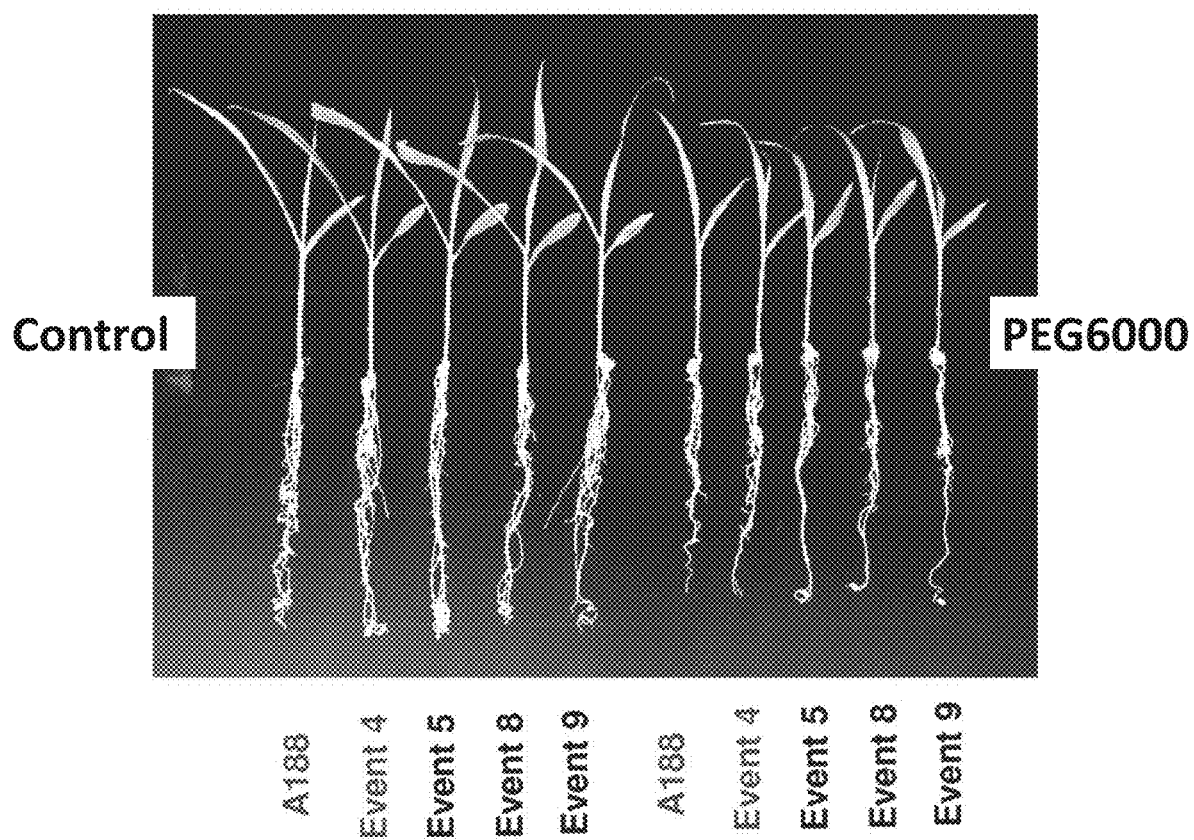

FIG. 9: Experiment 1: CrCIN maize seedlings under simulated drought stress: Photo of representative CrCIN plants after 2 days treatment with 25% PEG6000 versus control grow in ¼ strength Hoagland solution. All the plants were grown first for 1 week in ¼ strength Hoagland after germination before being transferred to the 25% PEG6000.

Figure 10:
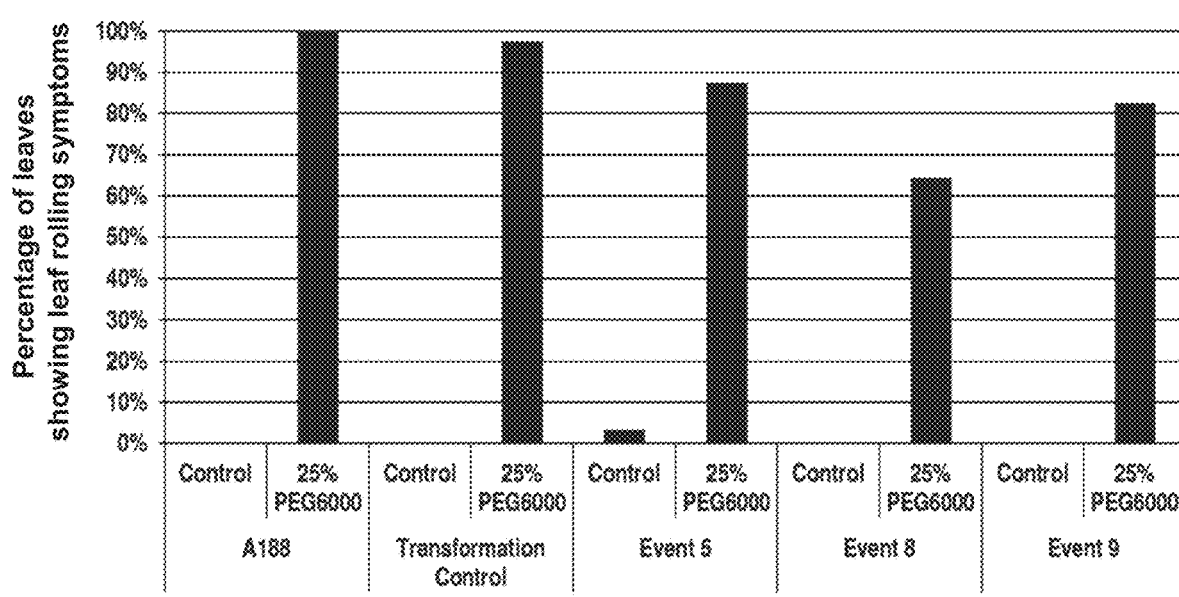

FIG. 10: Experiment 2: CrCIN maize seedlings under simulated drought stress: Graph displaying the percentage of leaves of 25% PEG6000 treated versus untreated plants (n=10) that showed leaf rolling symptoms of leaves. All plants were grown for 1 week in ¼ strength Hoagland Solution after germination and then treated for 1 day in added 25% PEG6000. Both control events showed high levels of leaf rolling, Event 5 and Event 9 showed reduced levels of leaf rolling and Event 8 showed a significant reduction in leaf rolling symptoms.

Figure 11:
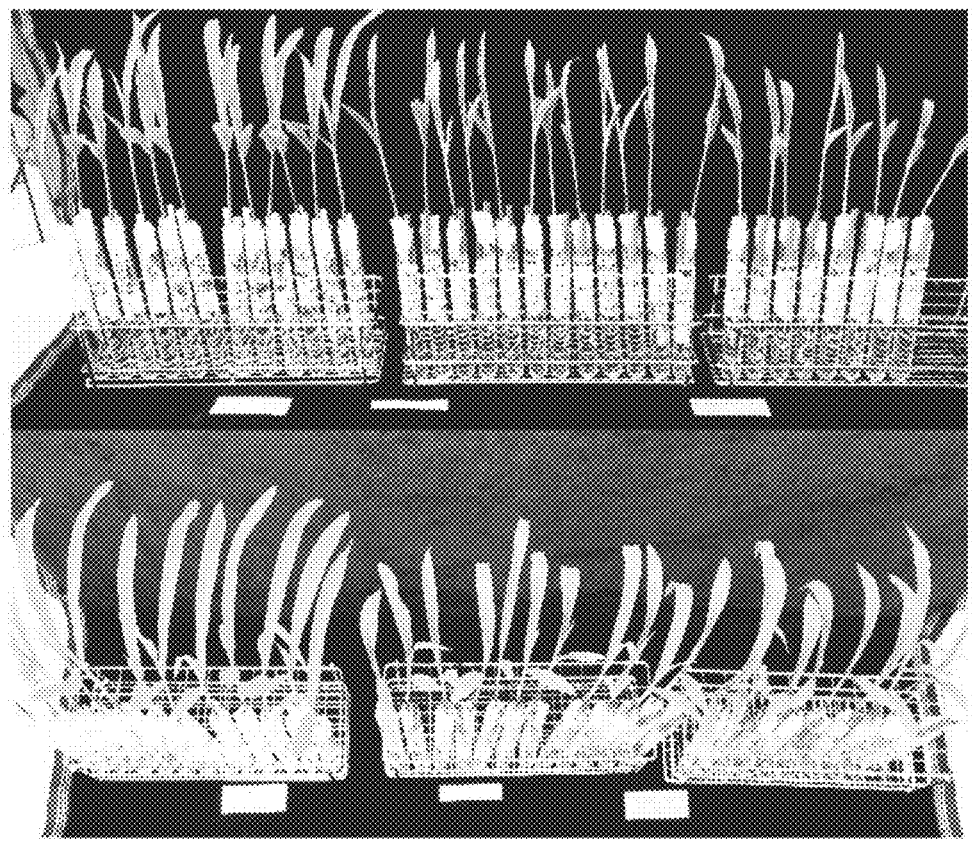

FIG. 11: Experiment 2: CrCIN maize seedlings under simulated drought stress: Photo of Event 8 CrCIN plants after 2 days treatment with 25% PEG6000. Here it can be seen that the leaves of Event 8 show less leaf rolling symptoms than the WT. All the plants were grown first for 1 week in ¼ strength Hoagland after germination before being transferred to the 25% PEG6000.

Figure 12:
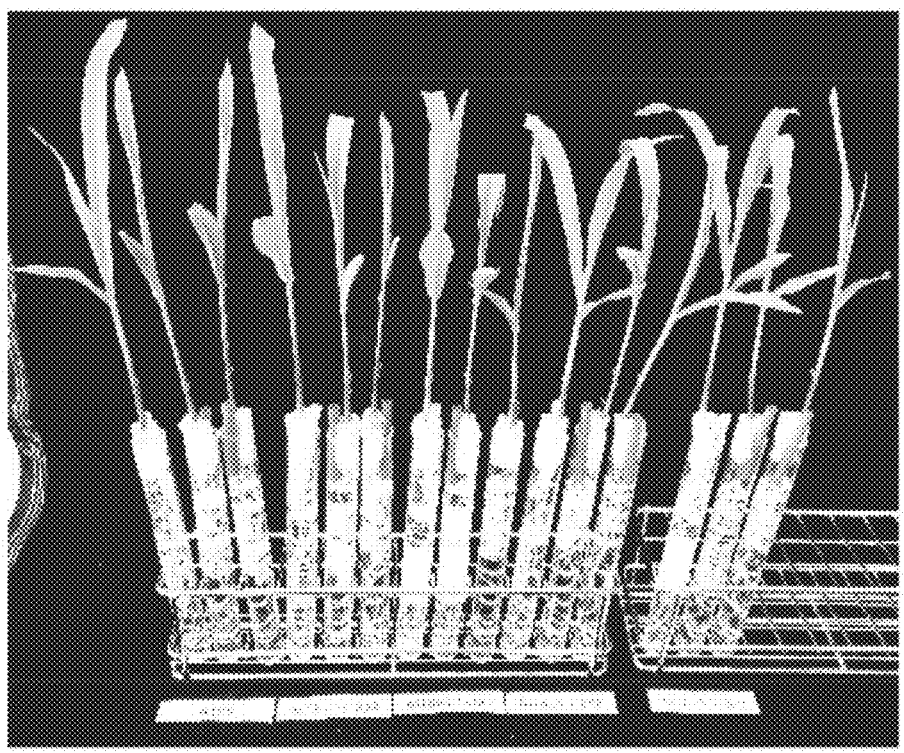

FIG. 12: Experiment 2: CrCIN maize seedlings under simulated drought stress: Photo of three representative CrCIN plants after 2 days treatment with 25% PEG6000. The biggest difference is the development of the 3rd leaf in Event 8 and Event 9 plants versus the controls. All the plants were grown first for 1 week in ¼ strength Hoagland after germination before being transferred to the 25% PEG6000.

Figure 13A:
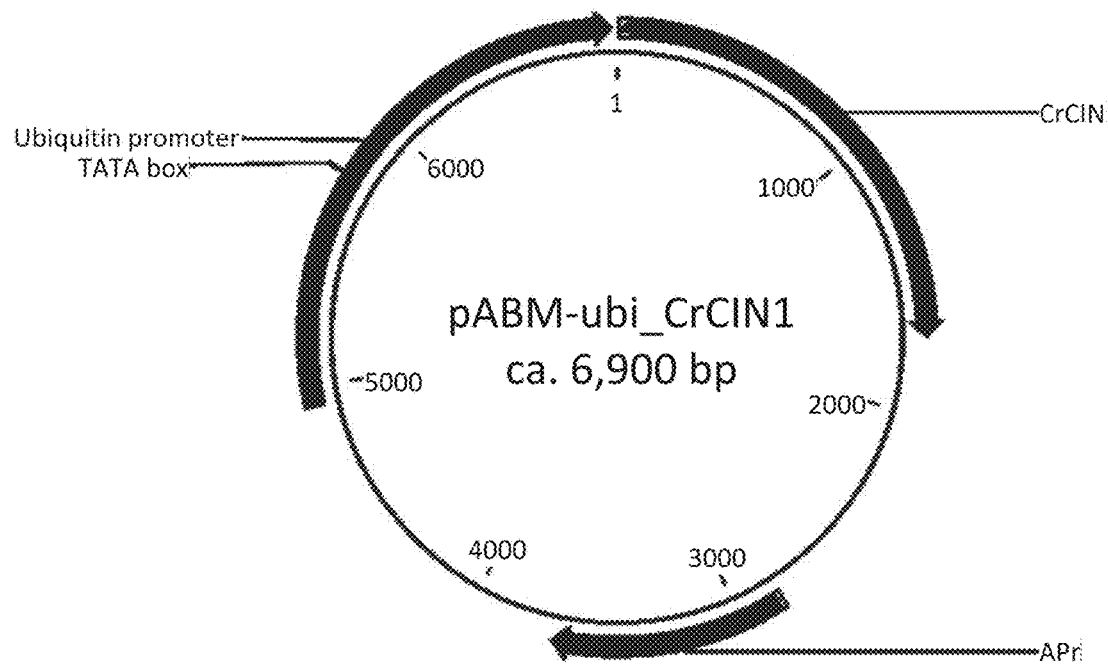
Figure 13B:
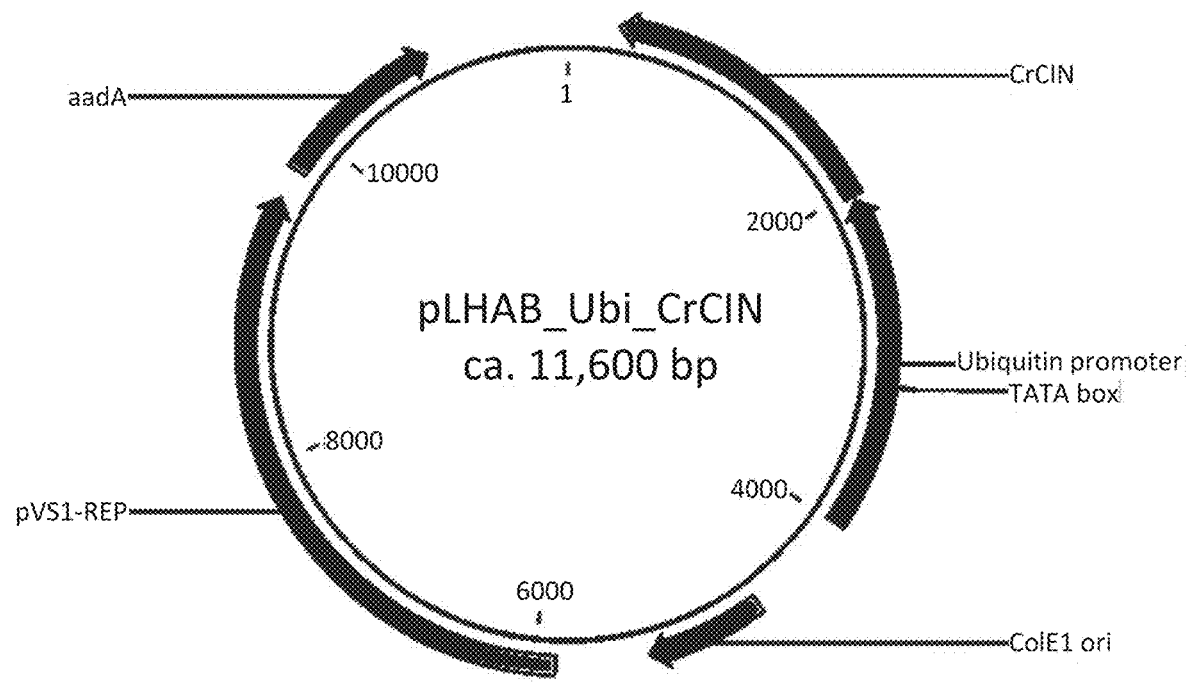

FIG. 13A-B: Data from wheat CrCIN transgenic plants: FIG. 13A: Plasmid map of wheat pABM-ubi-CrCIN (Apr_Ampicillin resistance) and FIG. 13B: Plasmid map of wheat pLHAB-ubi-CrCIN (aadA: Spectinomycin resistance, ColE1 ori: origin of replication for *E. coli*, pVS1 REP: origin of replication for *Agrobacterium*).

Figure 14:
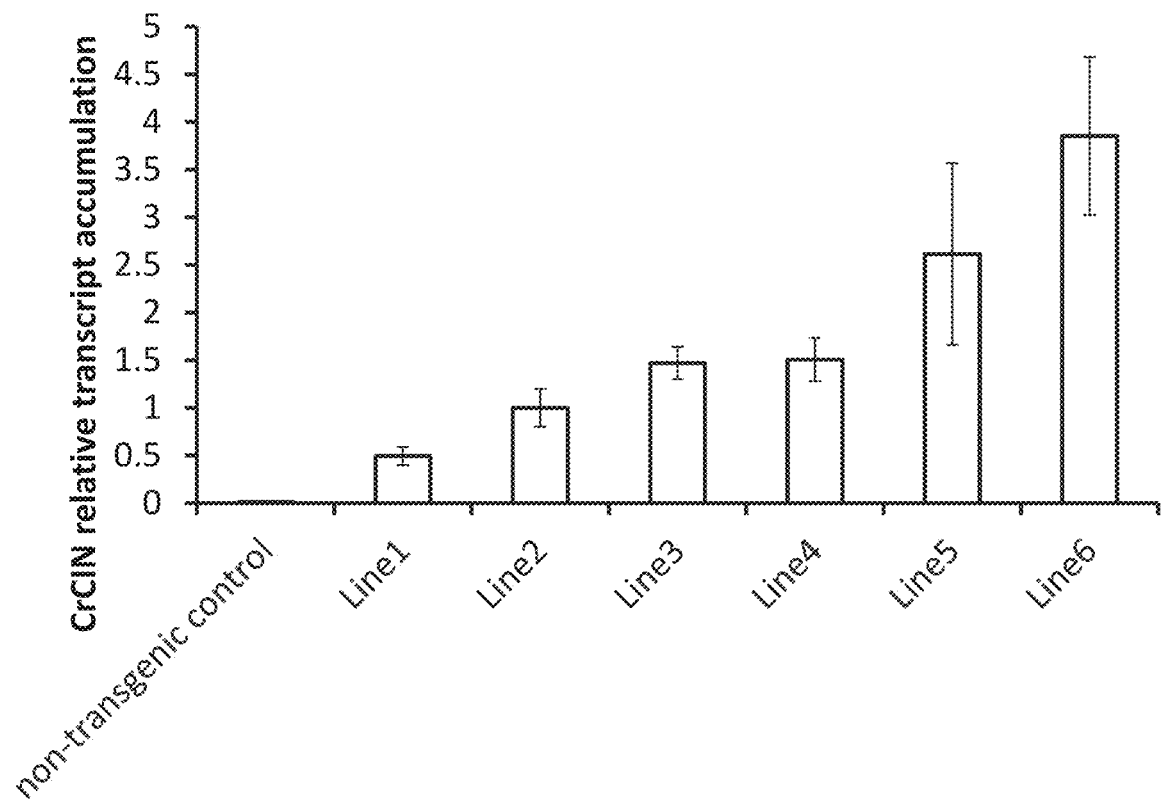

FIG. 14: Wheat: CrCIN T1 screening, CrCIN expression: Mean±SE. Five biological replicates were used. CrCIN expression was analyzed from leaves of four week old plants grown in the greenhouse. Expression of TaEF was used as internal control. All plants were fully randomized in the greenhouse.

Figure 15A:
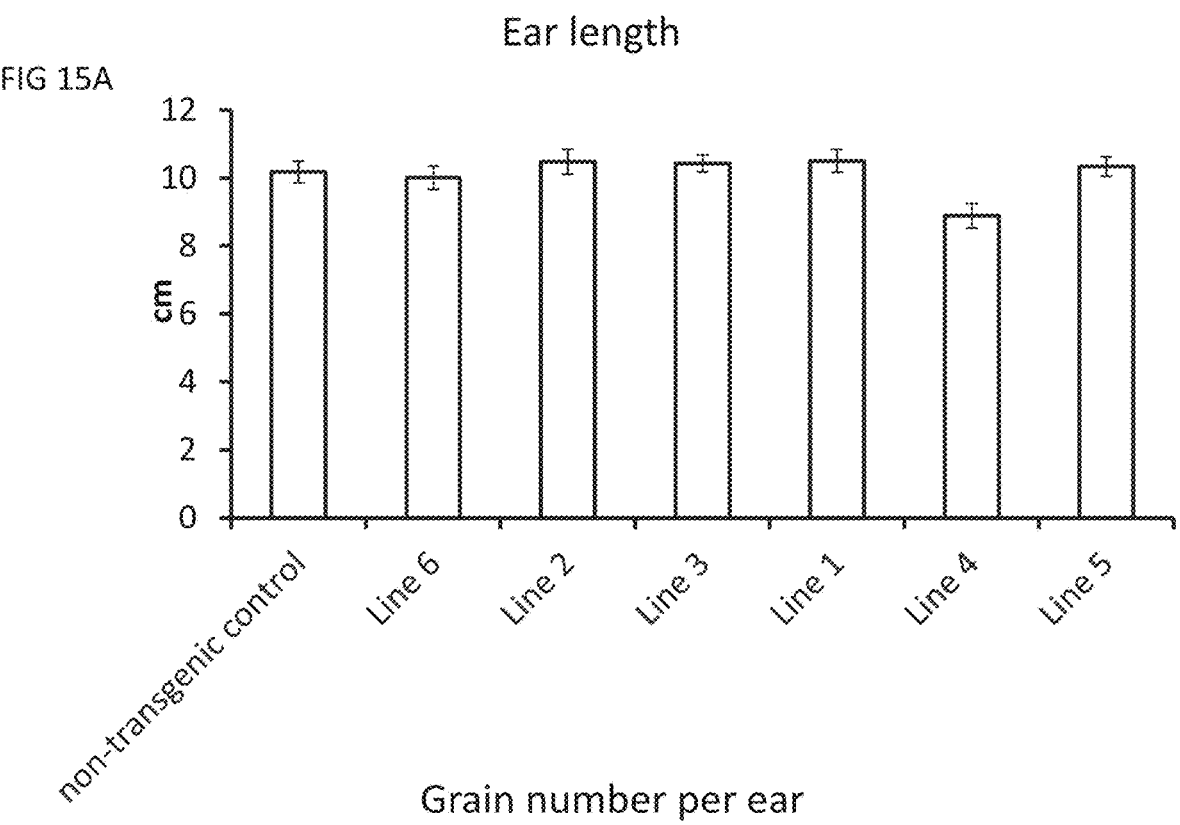
Figure 15B:
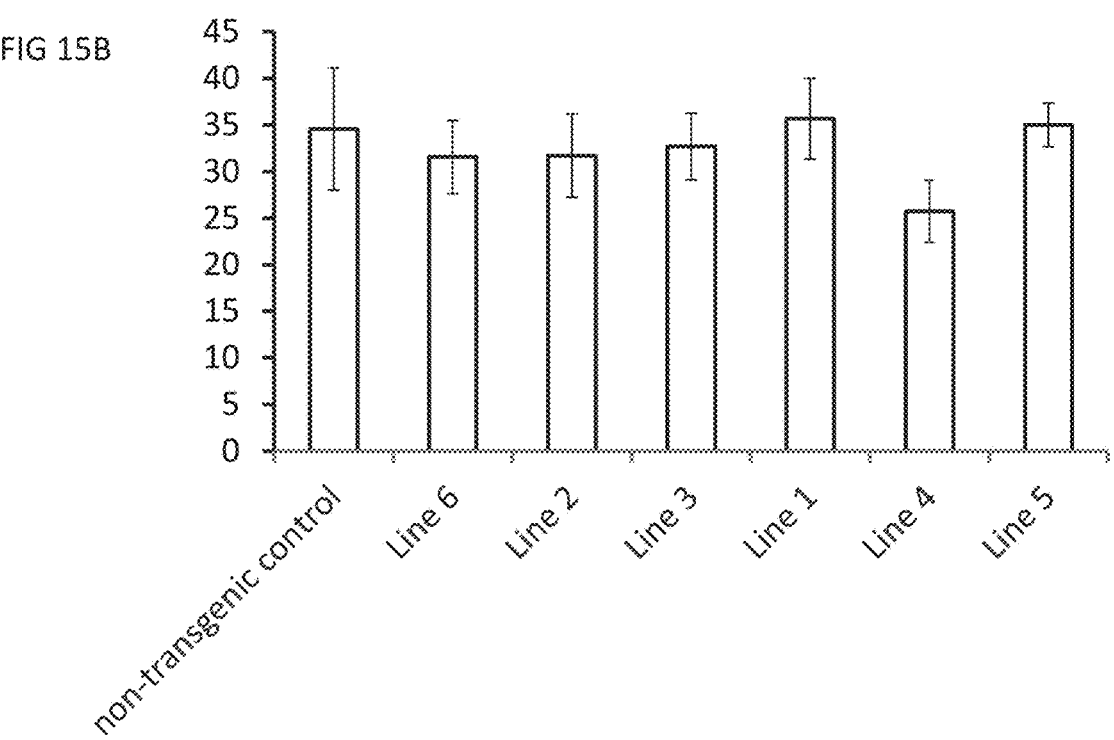
Figure 15C:
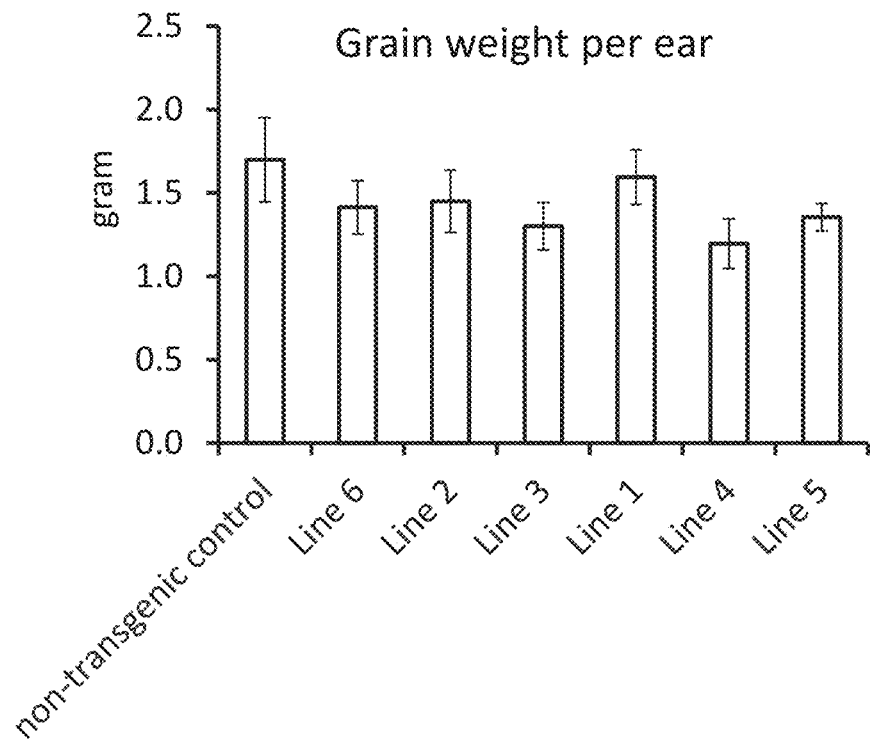
Figure 15D:
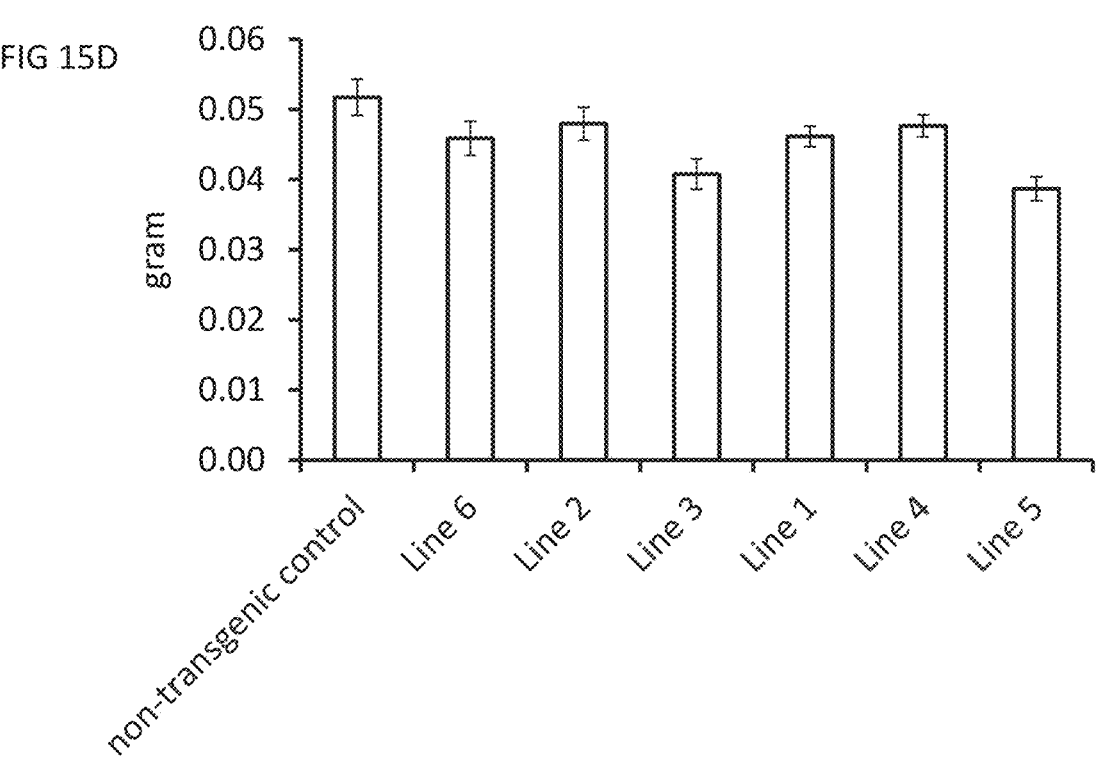

FIG. 15A-D: CrCIN overexpression does not increase yield or yield-related parameters in wheat in the greenhouse. FIG. 15A Ear length, FIG. 15B Grain number per ear, FIG. 15C Grain weight per ear and FIG. 15D Grain weight was measured on the 4 first matured tillers of greenhouse-grown plants. Shown are Means±Standard error, N≥10 biological replicates. Statistical analysis was done by Two-way Anova. Other growth parameters (e.g. plant height) also did not show any significant difference.

FIG. 16. CrCIN overexpression does not increase yield in the field. Numbers present yield in percentage of control plants (non-transgenic TAIFUN) at different locations. ANOVA analysis of single and multiple locations did not reveal any significant difference between transgenic CrCIN lines and control.

Figure 17:
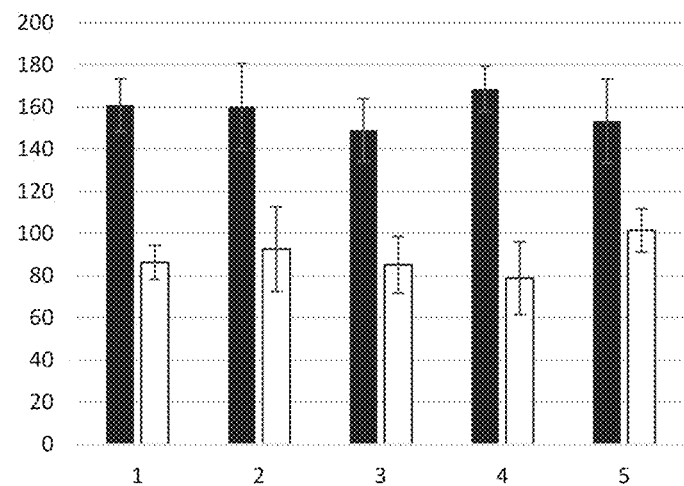
Figure 17:
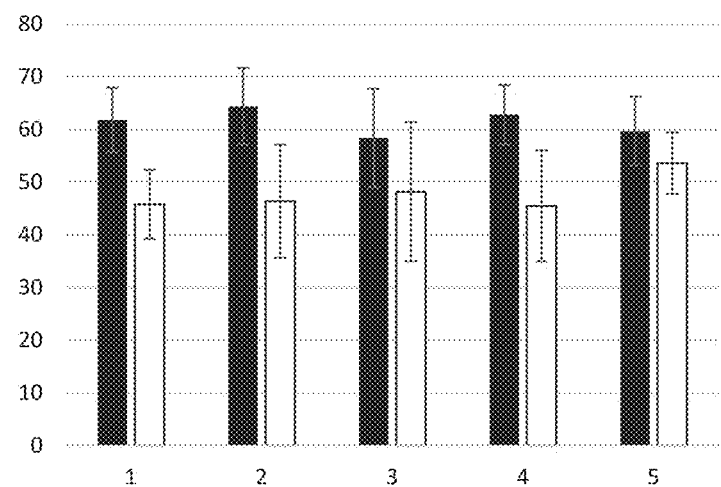

FIG. 17. CrCIN overexpression in wheat (TAIFUN) does not lead to a detectable drought tolerance phenotype neither with respect to the leaf dry mass (top panel) nor to the root dry mass (bottom panel). black column: control without drought stress; white column: with drought stress simulated by application of 10% PEG; 1, 2, 3: transgenic CrCIN lines with CrCIN overexpression; 5 and 6: lines without CrCIN overexpression (control).

EXAMPLES

Results with Transgenic Maize Plants

We first synthesized the *Chenopodium rubrum* cell wall invertase (CrCIN) gene and then transformed it into a shuttle vector cassette containing an ubiquitin promoter (containing an intron) from maize and a 35S terminator sequence to induce constitutive overexpression of the gene in a corn plant (FIGS. 1A and B). This cassette was then transformed into a binary vector containing for instance a herbicide gene (e.g.: BASTA resistance, glyphosate resistance or ALS inhibitor resistance) and spectinomycin resistance gene for subsequent transformation into *Agrobacterium tumefaciens* for *Agrobacterium* mediated plant transformation into maize (*Zea mays*) genotype A188 (FIG. 1C).

These subsequently transformed maize embryos were then selected by herbicide treatment and regenerated into plants for seed production in the greenhouse. From this seed batch T1 homozygous plants were grown. The expression levels of the regenerated homozygous T1 CrCIN plants have been determined by means of RT-qPCR displaying relative expression of selected CrCIN events to endogenous control gene ZmEF1 (FIG. 2). Both non-transformed A188 and the transformation control (A188 transformed with empty vector) showed no expression, while those A188-lines containing CrCIN as transgene showed CrCIN expression at different levels.

In addition, T1 homozygous plants were analyzed in the greenhouse for general physiological changes using primarily the leaf stage protocol comprising the counting of all leaves including the dead ones starting from the base of the plant to the first exposed leaf as per the Iowa State University protocol—also known as Leaf Collar Method (Abendroth et al., 2011, Corn Growth and Development, Iowa State University, Available Inventory: 9182).

The Leaf Collar Method determines leaf stage in corn by counting the number of leaves on a plant with visible leaf collars, beginning with the lowermost, short, rounded-tip true leaf and ending with the uppermost leaf with a visible leaf collar. The leaf collar is the light-colored collar-like "band" located at the base of an exposed leaf blade, near the spot where the leaf blade comes in contact with the stem of the plant. Leaves within the whorl, not yet fully expanded and with no visible leaf collar are not included in this leaf staging method. The exception to this statement may be that leaves with barely visible leaf collars can be counted when you are staging plants early in the day, recognizing that the leaf collar may become completely visible by the end of the day. Leaf stages are usually described as "V" stages, e.g., V2=two leaves with visible leaf collars. The leaf collar method is generally the most widely used method by university and industry agronomists in the US. Mass accumulation in the CrCIN plants was observed to increase from the V8 stage of growth until reproductive stage compared to the control plants in all events that showed expression (FIG. 3A). This was measured by counting the V stages of the plants where the transgenic plants had significantly more leaves than the control A188 plants (FIG. 4).

In one experiment, the plant height was also measured by bunching the leaves together and then pulling up and measuring plant height from the soil/plant stem base to the top of the tallest leaf (FIG. 5).

T2 homozygous seeds collected from these plants were then grown a second time and the biomass phenotype was reconfirmed by determining V stages at 8 weeks growth under greenhouse and field conditions (FIG. 6). Plant height was not measured again in the T2 plants as this could be clearly seen by eye (cf. FIG. 3B).

T2 seedlings were tested in a hydroponics experiment with 25% PEG6000 in 0.25× strength Hoagland solution to simulate drought stress (osmotic stress). Under such drought stress corn seedlings usually develop severe leaf dehydration and leaf rolling symptoms. Thus, leaf rolling in grasses like maize may be used as an estimate of obvious effects of water deficit (O'Toole, John C., and Rolando T. Cruz. "Response of leaf water potential, stomatal resistance, and leaf rolling to water stress." *Plant physiology* 65.3 (1980): 428-432.). Investigating the levels of leaf rolling the seedlings with CrCIN Events E5, E8 and E9 showed enhanced tolerance to PEG6000 application compared to control A188 plants and transformation control in replicated experiments (experiment 1: FIGS. 7-9; experiment 2: FIGS. 10-12). of T2 seedlings (FIGS. 7-12). In these experiments there seems to be a dosage effect with the highest expressing events showing the strongest phenotype. As can be seen from the experiments, all maize plants into which the CrCIN nucleic acid has been introduced and which express CrCIN produce an increased yield under normal and drought conditions and have the drought tolerant phenotype.

Negative Results with Transgenic Wheat Plants

CrCIN was overexpressed in wheat using an ubiquitin promotor (pABM-ubi-CrCIN and pLHAB-ubi-CrCIN; FIGS. 13A and B). Homozygous T1 plants were screened in the greenhouse. CrCIN expression was analyzed from leaves of four week old plants grown in the greenhouse. Expression of TaEF was used as internal control. All plants were fully randomized in the greenhouse. The non-transgenic control (TAIFUN transformed with empty vector) showed no expression, while those TAIFUN-lines containing CrCIN as transgene showed CrCIN expression at different levels. However, in contrast to the results observed in maize CrCIN overexpression in wheat surprisingly does not increase yield or yield-related parameters in the greenhouse. Even though different types of yield measurements have been executed, e.g., measuring plant height (data not shown), ear lengths (FIG. 15A), counting grain number per ear (FIG. 15B), measuring grain weight per ear (FIG. 15C) and grain weight measured on the 4 first matured tillers of greenhouse-grown plants, no significant difference have been determined. Measurements have been repeated with T2 and T3 lines in greenhouse and field. Field trials were done at 5 different locations with randomized complete block design (RCBD) in 4 replicates. even these trials revealed no significant difference in yield when compared to non-transgenic background TAIFUN (FIG. 16).

Furthermore, the CrCIN overexpression in wheat does not show a significant effect on potential drought tolerance in wheat. There is no detectable difference in leaf dry mass or root dry mass between CrCIN overexpression lines and control lines without CrCIN overexpression in response to drought stress by PEG application (FIG. 17).

The invention claimed is:

1. A transgenic maize plant comprising as transgene stably integrated into the genome of the maize plant:
   i) an expression cassette comprising a nucleic acid capable of expressing a *Chenopodium rubrum* cell wall invertase according to SEQ ID NO: 3,
   wherein the nucleic acid is constitutively overexpressed more than 10-fold relative to endogenous control gene ZmEF1, and
   wherein as a result of the constitutive overexpression of the cell wall invertase, the transgenic maize plant exhibits an enhanced tolerance to drought and an increased biomass yield, optionally as compared to a reference.

2. A plant cell, a tissue, a harvestable part, or a seed of the transgenic maize plant of claim 1, wherein the plant cell, the tissue, the part, or the seed comprises the transgene.

3. The transgenic maize plant of claim 1, wherein the expression of the nucleic acid is controlled by a constitutive promoter, optionally comprising one or more promoter regulatory sequences and/or one or more terminator regulatory sequences.

4. A method of producing the transgenic maize plant of claim 1, comprising the following steps:
   introducing into at least a cell of a maize plant the expression cassette according to claim 1, or a vector comprising the expression cassette, and
   regenerating the transgenic maize plant from the at least a cell.

5. A method of enhancing the drought tolerance of a maize plant and of increasing biomass yield potential of a maize plant, comprising the following steps:
   introducing into at least a cell of a maize plant expression cassette according to claim 1, or a vector comprising the expression cassette, and
   causing constitutive overexpression of more than 10-fold relative to endogenous control gene ZmEF1.

6. A vector comprising the expression cassette according to claim 1.

7. A method for production of ethanol or methane comprising the following steps:
   cutting the transgenic maize plant according to claim 1,
   optionally treating the cut maize plant with an ensilage agent,
   optionally storing the cut maize plant optionally treated with an ensilage agent, and
   producing ethanol or methane from the cut maize plant by anaerobic digestion.

8. A method for production of ethanol or methane comprising the following steps:
   cutting the harvestable part according to claim 2,
   optionally treating the cut harvestable part with an ensilage agent,
   optionally storing the cut harvestable part optionally treated with an ensilage agent, and
   producing ethanol or methane from the cut harvestable part by anaerobic digestion.

* * * * *

SEQUENCE LISTING

```
Sequence total quantity: 5
SEQ ID NO: 1             moltype = DNA   length = 1722
FEATURE                  Location/Qualifiers
source                   1..1722
                         mol_type = unassigned DNA
                         organism = Chenopodium rubrum
SEQUENCE: 1
atggcttcct ataagttacc aaaacaagtg attttgttac ttgtttctct cctcttcttc   60
tgctatggcg ttgttgagct tcaagccgcg caatctccac cttcgaatca accttatcga  120
acggcctacc attttcaacc acgcaaaaac tggatcaacg atcctaatgg accaatgcta  180
ttcaaaggca tataccacct attttatcaa tacaacccta atggtgtaaa attacggggt  240
ccgccggtgt ggggtcactc aacctcaaag gatctagtaa actggatgcc acaaccatta  300
acaatggagc agaaatggca agccaacatt aatggaagtt ggtcgggttc agccactata  360
ctcccaggaa ataaaccggc aattctcttt actggacttg acccaaatta tgaacaagtc  420
caagttttag cctaccctaa agatttaaat gacccttatc ttaaagaatg gttttttggca  480
ccaaaaaatc cagtcatgtt ccctacccca cagaatcaaa tcaatgccac ctcgtaccgg  540
gacccaacga cagcgtggat gctgccagat ggcaattgga gagtgctcat ggaaagtcc   600
aaaaggagag agcgtggatt gtccttatta tatagaagca gagattttgt tcattgggtt  660
aaagctaaac acccttata ttcttatgaa cgtagtggca tgtgggaatg tcccgatttt   720
ttccctgttt ataaaaacgg taacacaatg ggtatagata cgtctgtaat tggtcctaat  780
attaagcatg tactcaaagt tagccttgat gtaagtaagc atgatgttta tacaattgga  840
ggatatgata ctaagaagga tgcgtatact cctgatgtgg gtttcatgaa cgactcgagt  900
ttaaggtatg attatggtaa atattacgcc tccaagacat tttacgacgg tgctaagaaa  960
gagaggattt tgcttggttg ggctaatgag tcttcgagtg aggaagatga cgctaaaaag 1020
ggatggtctg ggattcacac tattccaaga acgatttggc ttgacaaatc agggaaccag 1080
ttgattcaat ggccaatttc aaatattgaa aaattgagac aaaaatcccc agtgttcaaa 1140
ttatacggca aattaatcaa aggaggttca ctaaatgaag tgtctggcat tactgcagca 1200
caggcagata tagaaatatc attcaaaatc aaggacttga agatgtgaa gaagtttgat 1260
gcaagttgga ctaacccaca gctgctttgt agccaaaagg gtggctcagt caaaggtggg 1320
ctcggaccgt ttgggttgat gacttttcag gcttccaagg gttagaaga gtatacagct 1380
gtcttttca gaattttcaa agcctatgac aataaatatg tggtccttat gtgcagtgac 1440
caaagcaggt cttctctgaa tccgacaaat gacaaaacaa cttatggatc ttttgtggat 1500
gttaatcctg ttcgtgaaga tctgtccttg agagttttga ttgatcattc agtggtggag 1560
agctttggag caaaaggaa agaatgtgta acagcaagag tttatccac attggcaatt 1620
aatgaaaagg cttgcaattt atatgtcttc aacaacggga atcagatgt tgagatcact 1680
ggattaacag cttggagcat gaagaaagct tctattgctt aa                    1722

SEQ ID NO: 2             moltype = AA   length = 573
FEATURE                  Location/Qualifiers
source                   1..573
                         mol_type = protein
                         organism = Chenopodium rubrum
SEQUENCE: 2
MASYKLPKQV ILLLVSLLFF CYGVVELQAA QSPPSNQPYR TAYHFQPRKN WINDPNGPML   60
FKGIYHLFYQ YNPNGVKLRG PPVWGHSTSK DLVNWMPQPL TMEPEMAANI NGSWSGSATI  120
LPGNKPAILF TGLDPNYEQV QVLAYPKDLN DPYLKEWFLA PKNPVMFPTP QNQINATSYR  180
DPTTAWMLPD GNWRVLIGKS KRRQRGLSLL YRSRDFVHWV KAKHPLYSYE RSGMWECPDF  240
FPVVKNGNTM GIDTSVIGPN IKHVLKVSLD VSKHDVYTIG GYDTKKDAYT PDVGFMNDSS  300
LRYDYGKYYA SKTFYDGAKK ERILLGWANE SSSEEDDAKK GWSGIHTIPR TIWLDKSGNQ  360
LIQWPISNIE KLRQKSPVFK LYGKLIKGGS LNEVSGITAA QADVEISFKI KDLENVEKFD  420
ASWTNPQLLC SQKGGSVKGG LGPFGLMTFQ ASKGLEEYTA VFFRIFKAYD NKYVVLMCSD  480
QSRSSLNPTN DKTTYGSFVD VNPVREDLSL RVLIDHSVVE SFGAKRKECV TARVYPTLAI  540
NEKACNLYVF NNGKSDVEIT GLTAWSMKKA SIA                              573

SEQ ID NO: 3             moltype = DNA   length = 1722
FEATURE                  Location/Qualifiers
source                   1..1722
                         mol_type = other DNA
                         organism = synthetic construct
                         note = codon optimized sequence for expression of CrCIN in
                         maize
SEQUENCE: 3
atggcttcct ataagttacc aaaacaagtg attttgttac ttgtttctct cctcttcttc   60
tgctatggcg ttgttgagct tcaagccgcg caatctccac cttcgaatca accttatcga  120
acggcctacc attttcaacc acgcaaaaac tggatcaacg atcctaatgg accaatgcta  180
ttcaaaggca tataccacct attttatcaa tacaacccta atggtgtaaa attacggggt  240
ccgccggtgt ggggtcactc aacctcaaag gatctagtaa actggatgcc acaaccatta  300
acaatggagc agaaatggca agccaacatt aatggaagtt ggtcgggttc agccactata  360
ctcccaggaa ataaaccggc aattctcttt actggacttg acccaaatta tgaacaagtc  420
caagttttag cctaccctaa agatttaaat gacccttatc ttaaagaatg gttttttggca  480
ccaaaaaatc cagtcatgtt ccctacccca cagaatcaaa tcaatgccac ctcgtaccgg  540
gacccaacga cagcgtggat gctgccagat ggcaattgga gagtgctcat ggaaagtcc   600
aaaaggagag agcgtggatt gtccttatta tatagaagca gagattttgt tcattgggtt  660
aaagctaaac acccttata ttcttatgaa cgtagtggca tgtgggaatg tcccgatttt   720
ttccctgttt ataaaaacgg taacacaatg ggtatagata cgtctgtaat tggtcctaat  780
attaagcatg tactcaaagt tagccttgat gtaagtaagc atgatgttta tacaattgga  840
ggatatgata ctaagaagga tgcgtatact cctgatgtgg gtttcatgaa cgactcagt   900
ttaaggtatg attatggtaa atattacgcc tccaagacat tttacgacgg tgctaagaaa  960
```

```
gagaggattt tgcttggttg ggctaatgag tcttcgagtg aggaagatga cgctaaaaag  1020
ggatggtctg ggattcacac tattccaaga acgatttggc ttgacaaatc agggaaccag  1080
ttgattcaat ggccaatttc aaatattgaa aaattgagac aaaaatcccc agtgttcaaa  1140
ttatacggca aattaatcaa aggaggttca ctaaatgaag tgtctggcat tactgcagca  1200
caggcagatg tagaaatatc attcaaaatc aaggacttgg agaatgtgga gaagtttgat  1260
gcaagttgga ctaacccaca gctgctttgt agccaaaagg gtggctcagt caaaggtggg  1320
ctcggaccgt ttgggttgat gacttttcag gcttccaagg gtttagaaga gtatacagct  1380
gtcttttca gaattttcaa agcctatgac aataaatatg tggtccttat gtgcagtgac  1440
caaagcaggt cttctctgaa tccgacaaat gacaaaacaa cttatggatc ttttgtggat  1500
gttaatcctg ttcgtgaaga tctgtccttg agagttttga ttgatcattc agtggtggag  1560
agctttggag caaaaaggaa agaatgtgta acagcaagag tttatcccac attggcaatt  1620
aatgaaaagg cttgcaattt atatgtcttc aacaacggga atcagatgt tgagatcact  1680
ggattaacag cttggagcat gaagaaagcg tctattgctt aa                     1722

SEQ ID NO: 4             moltype = AA   length = 573
FEATURE                  Location/Qualifiers
source                   1..573
                         mol_type = protein
                         organism = synthetic construct
                         note = protein encoded by codon optimized DNA sequence of
                           SEQ ID NO: 3
SEQUENCE: 4
MASYKLPKQV ILLLVSLLFF CYGVVELQAA QSPPSNQPYR TAYHFQPRKN WINDPNGPML   60
FKGIYHLFYQ YNPNGVKLRG PPVWGHSTSK DLVNWMPQPL TMEPEMAANI NGSWSGSATI  120
LPGNKPAILF TGLDPNYEQV QVLAYPKDLN DPYLKEWFLA PKNPVMFPTP QNQINATSYR  180
DPTTAWMLPD GNWRVLIGKS KRRQRGLSLL YRSRDFVHWV KAKHPLYSYE RSGMWECPDF  240
FPVYKNGNTM GIDTSVIGPN IKHVLKVSLD VSKHDVYTIG GYDTKKDAYT PDVGFMNDSS  300
LRYDYGKYYA SKTFYDGAKK ERILLGWANE SSSEEDDAKK GWSGIHTIPR TIWLDKSGNQ  360
LIQWPISNIE KLRQKSPVFK LYGKLIKGGS LNEVSGITAA QADVEISFKI KDLENVEKFD  420
ASWTNPQLLC SQKGGSVKGG LGPFGLMTFQ ASKGLEEYTA VFFRIFKAYD NKYVVLMCSD  480
QSRSSLNPTN DKTTYGSFVD VNPVREDLSL RVLIDHSVVE SFGAKRKECV TARVYPTLAI  540
NEKACNLYVF NNGKSDVEIT GLTAWSMKKA SIA                              573

SEQ ID NO: 5             moltype = DNA   length = 1952
FEATURE                  Location/Qualifiers
source                   1..1952
                         mol_type = genomic DNA
                         organism = Chenopodium rubrum
SEQUENCE: 5
gcattaatat tcacatccat tattcatggc ttcctataag ttaccaaaac aagtgatttt   60
gttacttgtt tctctcctct tcttctgcta tggcgttgtt gagcttcaag ccgcgcaatc  120
tccaccttcg aatcaacctt atcgaacggc ctaccatttt caaccacgca aaaactggat  180
caacgatcct aatggaccaa tgctattcaa aggcatatac cacctatttt atcaatacaa  240
ccctaatggt gtaaaattac ggggtccgcc ggtgtgtggg cactcaacct caaaggatct  300
agtaaactgg atgccacaac cattaacaat ggagccagaa atggcagcca acattaatgg  360
aagttggtcg ggttcagcca ctatactccc aggaaataaa ccggcaattc tcttttactgg  420
acttgaccca aattatgaac aagtccaagt tttagcctac cctaaagatt taaatgaccc  480
ttatcttaaa gaatggtttt tggcaccaaa aaatccagtc atgttcccta ccccacagaa  540
tcaaatcaat gccacctcgt accgggaccc aacgacagcg tggatgctgc cagatggcaa  600
ttggagagtg ctcattggaa agtccaaaag agacagcgt ggattgtcct tattatatag   660
aagcagagat tttgttcatt gggttaaagc taaacaccct ttatattctt atgaacgtag  720
tggcatgtgg gaatgtccg attttttccc tgtttataaa aacggtaaca caatgggtat  780
agatacgtct gtaattggtc ctaatattaa gcatgtactc aaagttagct tagatgtaag  840
taagcatgat gtttatacaa ttggaggata tgatactaag aaggatgcgt atactcctga  900
tgtgggtttc atgaacgact cgagtttaag gtatgattat ggtaaatatt acgcctccaa  960
gacattttac gacggtgcta agaaagagag gattttgctt ggttgggcta atgagtcttc  1020
gagtgaggaa gatgacgcta aaagggatg gtctgggatt cacactattc caagaacgat  1080
ttggcttgac aaatcaggga accagttgat tcaatggcca atttcaaata ttgaaaaatt  1140
gagacaaaaa tccccagtgt tcaaattata cggcaaatta atcaaaggag gttcactaaa  1200
tgaagtgtct ggcattactg cagcacaggc agatgtagaa atatcattca aaatcaagga  1260
cttggagaat gtggagaagt ttgatgcaag ttggactaac ccacagctgc tttgtagcca  1320
aaagggtggc tcagtcaaag gtgggctcgg accgtttggg ttgatgactt ttcaggcttc  1380
caagggttta gaagagtata gctgtctt tttcagaatt tcaaagcct atgacaataa  1440
atatgtggtc cttatgtgca gtgaccaaag caggtcttct ctgaatccga caaatgacaa  1500
aacaacttat ggatcttttg tggatgttaa tcctgttcgt gaagatctgt ccttgagagt  1560
tttgattgat cattcagtgg tggagagctt tggagcaaaa aggaaagaat gtgtaacagc  1620
aagagtttat cccacattgg caattaatga aaaggcttgc aatttatatg tcttcaacaa  1680
cgggaaatca gatgttgaga tcactggatt aacagcttgg agcatgaaga aagcttctat  1740
tgcttaactc aaattaaatt agctcattca aaaatcaatt tcgccgatt tagaggaat   1800
atatgatgat aattattgca ttcattcaca taatttatg tagttttttt cgttgattga  1860
agagtacaat catgtacaca gtggaacaca cagtagtagg aaaatgtcaa tgtatatttt  1920
tcttcggaat taattaatac tgagtaaaaa gc                               1952
```